(12) United States Patent
Ralph

(10) Patent No.: US 9,050,352 B2
(45) Date of Patent: Jun. 9, 2015

(54) IMMUNOMODULATING COMPOSITIONS AND USES THEREFOR

(76) Inventor: Stephen John Ralph, Mermaid Waters (AU)

(*) Notice: Subject to any disclaimer, the term of this patent is extended or adjusted under 35 U.S.C. 154(b) by 1693 days.

(21) Appl. No.: 10/575,813

(22) PCT Filed: Oct. 18, 2004

(86) PCT No.: PCT/AU2004/001429
§ 371 (c)(1),
(2), (4) Date: Jan. 3, 2007

(87) PCT Pub. No.: WO2005/037293
PCT Pub. Date: Apr. 28, 2005

(65) Prior Publication Data
US 2007/0207161 A1    Sep. 6, 2007

Related U.S. Application Data

(60) Provisional application No. 60/511,745, filed on Oct. 16, 2003.

(51) Int. Cl.
| | | |
|---|---|---|
| A61K 31/7016 | (2006.01) | |
| A61K 31/715 | (2006.01) | |
| A61K 39/00 | (2006.01) | |
| A61K 39/39 | (2006.01) | |
| A61K 45/06 | (2006.01) | |
| G01N 33/50 | (2006.01) | |
| A61K 38/17 | (2006.01) | |
| A61K 38/19 | (2006.01) | |
| A61K 38/20 | (2006.01) | |

(52) U.S. Cl.
CPC ........... *A61K 31/7016* (2013.01); *A61K 31/715* (2013.01); *A61K 39/0011* (2013.01); *A61K 39/39* (2013.01); *A61K 45/06* (2013.01); *A61K 2039/5152* (2013.01); *A61K 2039/5154* (2013.01); *A61K 2039/5156* (2013.01); *A61K 2039/55583* (2013.01); *G01N 33/5047* (2013.01); *G01N 33/505* (2013.01); *G01N 2333/42* (2013.01); *G01N 2333/4724* (2013.01); *A61K 38/1774* (2013.01); *A61K 38/191* (2013.01); *A61K 38/193* (2013.01); *A61K 38/2066* (2013.01)

(58) Field of Classification Search
CPC ................................................. A61K 31/7016
See application file for complete search history.

(56) References Cited

U.S. PATENT DOCUMENTS

| | | | |
|---|---|---|---|
| 4,152,423 A | | 5/1979 | Adam et al. |
| 4,710,378 A | | 12/1987 | Ohtomo et al. |
| 5,580,756 A | | 12/1996 | Linsley et al. |
| 5,587,460 A | * | 12/1996 | Nedwin et al. ................. 530/396 |
| 5,609,871 A | | 3/1997 | Michael et al. |
| 5,783,193 A | | 7/1998 | Michael et al. |
| 6,328,972 B1 | * | 12/2001 | Rock ........................ 424/196.11 |
| 6,835,806 B2 | | 12/2004 | Chang |
| 2002/0107222 A1 | | 8/2002 | Platt |
| 2003/0013681 A1 | | 1/2003 | Chang et al. |
| 2003/0064957 A1 | | 4/2003 | Klyosov et al. |

FOREIGN PATENT DOCUMENTS

| | | |
|---|---|---|
| EP | 1 219 630 | 7/2002 |
| WO | 9704195 | 2/1997 |
| WO | 9727872 | 8/1997 |
| WO | 9954466 | 10/1999 |
| WO | WO 00/63251 A1 | 10/2000 |
| WO | 0141240 A2 | 6/2001 |
| WO | 0188097 A1 | 11/2001 |
| WO | 0207813 A1 | 1/2002 |
| WO | 0213858 | 2/2002 |
| WO | WO 02/50119 A2 | 6/2002 |
| WO | 02057284 | 7/2002 |
| WO | 2003065977 | 8/2003 |
| WO | WO 2004/041292 A2 | 5/2004 |

OTHER PUBLICATIONS

Tanasienko et al (Exp. Oncol. vol. 32, No. 4, pp. 254-257, 2010).*
Lombardi (Biochimica et Biophysica acta vol. 649, No. 3, pp. 661-679, 1981).*
Fukumori, T. et al. 2003 "CD29 and CD7 mediate galectin-3-induced type II T-cell apoptosis" *Cancer Research* 63:8302-8311.
Lantéri, M. et al. 2003 "Altered T cell surface glycosylation in HIV-1 infection results in increased susceptibility to galectin-1-induced cell death" *Glycobiology* 13:909-918.
Perillo, N.L. et al. 1995 "Apoptosis of T cells mediated by galectin-1" *Nature* 378:736-739.

(Continued)

*Primary Examiner* — Albert Navarro
(74) *Attorney, Agent, or Firm* — Knobbe, Martens, Olson & Bear, LLP

(57) ABSTRACT

The present invention discloses immunomodulating compositions. More particularly, the present invention discloses compositions comprising an immune-modulating agent and a lectin-interactive agent, which are useful for stimulating and prolonging host immune cell responses. The compositions of the present invention are particularly useful in the treatment and/or prophylaxis of a range of conditions including pathogenic infections, autoimmune diseases, transplant rejection, graft versus host disease, allergies, inflammatory disease, as well as cancers and tumours.

34 Claims, 4 Drawing Sheets

(56) References Cited

OTHER PUBLICATIONS

Rabinovich, G.A. et al. 2002 "Unlocking the secrets of galectins: a challenge at the frontier of glyco-immunology" *J Leukocyte Biology* 71:741-752.

GenBank extract for human galectin-1 (NCBI Accession No. NP_002296) retrieved from "http://www.ncbi.nlm.nih.gov/protein/NP_002296.1" on Aug. 8, 2013.

Perillo, et al., "Apoptosis of T cells mediated by galectin-1", Nature, vol. 378, Dec. 14, 1995, 6558; ProQuest, p. 736-739.

Allen, J. R. et al., 2001 "Pursuit of Optimal Carbohydrate-Based Anticancer Vaccines: Preparation of Multiantigenic Unimolecular Glycopeptide Containing the Tn, MBri, and Lewis Antigens", J. Am. Chem. Soc. 123: 1890-1897.

Apostolopoulous, V. et al., 1998 "MUCI cross-reactive Gala(1,3)Gal antibodies in humans switch immune responses from cellular to humoral" Nature Medicine 4(3): 315-320.

Dobroff, A. S. et al., 2002 "Protective, Anti-Tumor Monoclonal Antibody Recognizes a Conformational Epitope Similar to Melibiose at the Surface of Invasive Murine Melanoma Cells" Hybridoma and Hybridomics 21 (5): 321-331.

Faas et al., 2000 "Primary Structure and Functional Characterization of a Soluble Alternatively Spliced Form of B7-1" J. Immunol. 164(12): 6340-6348.

Geijtenbeek et al., 2002 "Mycobacteria Target DC-SIGN to Suppress Dendritic Function" Journal of Experimental Medicine 197(1): 7-17.

Ichim, T. E. et al., 2003 "Prevention of allograft rejection by in vitro generated tolerogenic dendritic cells" Transplant Immunology 11: 295-306.

Jeannin et al., 2000 "Soluble CD86 Is a Costimulatory Molecule for Human T Lymphocytes" Immunity 13(3): 303-312.

McHugh et al., 1998 "Detection of a Soluble Form of B7-1 (CD80) is Synovial Fluid from Patents with Arthritis Using Monoclonal Antibodies against Distinct Epitopes of Human B7-1" Clin. Immunol. Immunopathol. 87(1): 50-59.

Nishimura, T. et al., 2000 "The critical role of Th I-dominant immunity in tumour immunology" Cancer Chemother Pharmaco146, (Suppl): S52-S61.

Paulsson, K. et al., 2003 "Chaperones and folding of MHC class I molecules in the endoplasmic reticulum" Biochimica et Biophysica Acta 1641: 1-12.

Schroedl et al., 2003 "C-Reactive Protein and Antibacterial Activity in Blood Plasma of Colostrum-Fed Calves and the Effect of Lactulose" J. Dairy Sci. 86 3313-3320.

Schwarz, F. P. et al., 1998 "Thermodynamics of Bovine Spleen Galectin-I Binding to Disaccharides: Correlation with Structure and Its Effect on Oiigomerization at the Denaturation Temperature" Biochemistry 37: 5867-5877.

Sturrnhoefel et al., 1999 "Potent Activity of Soluble B7-IgG Fusion Proteins in Therapy of Established Tumors and as Vaccine Adjuvant" Cancer Res. 59: 4964-4972.

URL: http://www.jn-vaccines.org/Vaccines/NmVacAC.pdf., 2007, JN-International, Inc.

\* cited by examiner

US 9,050,352 B2

IMMUNOMODULATING COMPOSITIONS AND USES THEREFOR

This application is a U.S. National Phase of International Application No. PCT/AU2004/001429, filed Oct. 18, 2004 designating the U.S., and published in English as WO 2005/037293 on Apr. 28, 2005, which claims priority to U.S. Provisional Application 60/511,745, filed Oct. 16, 2003.

FIELD OF THE INVENTION

THIS INVENTION relates generally to immunomodulating compositions. More particularly, the present invention is directed to compositions comprising an immune-modulating agent and a lectin-interactive agent, which are useful for stimulating and prolonging host immune cell responses. The compositions of the present invention are particularly useful in the treatment and/or prophylaxis of a range of conditions including pathogenic infections, autoimmune diseases, transplant rejection, graft versus host disease, allergies, inflammatory disease, as well as cancers and tumours.

Bibliographic details of certain publications referred to by author in this specification are collected at the end of the description.

BACKGROUND OF THE INVENTION

According to one theory, much of the physiological decline of immune responses or homeostasis, is due to programmed death of lymphocytes resulting from the loss of survival signals. As antigens are eliminated, the clones of lymphocytes that were activated by the antigen are deprived of the essential survival stimuli and die by apoptosis. Survival stimuli for lymphocytes function mainly by inducing the expression of anti-apoptotic proteins.

Examples of animal lectins include the galectins (reviewed in Rabinovich et al., 2002, Trends Immunol. 23:313-320; Rabinovich et al., J Leuk Biol 2002, 71: 741-752) or LGALS1 (lectin, galactoside-binding, soluble Blaser C. et al., *Euro. J Immunol*, 1998, 28: 2311-2319). The galectins, as a family of galactoside binding proteins have potent immunoregulatory activity (reviewed in Rabinovich et al., *J Leuk Biol.*, 2002, 71: 741-752). In particular, galactin-1 is a negative regulator of T-cell responses, inducing apoptosis of T cells (Perillo, N L et al., *Nature*, 1995, 378(6558):736-739). Galectin-1 is also secreted by activated T cells thereby acting as a self regulator of T cell activation inhibiting antigen-induced proliferation of T cells (Blaser, C et al., as above).

In work leading up to the present invention, the inventor surprisingly discovered that lactulose significantly improves the efficacy of raising and prolonging an immune response to a selected antigen. Not wishing to be bound by any one particular theory or mode of operation, these surprising results are believed to be based at least in part on the ability of a lectin-interactive agent such as lactulose competing with the glycoprotein receptors on the surface of T cells for binding to lectin, thereby inhibiting lectin-induced glycoprotein receptor clustering on the surface of T cells and preventing or attenuating the inhibition of T cell activation.

SUMMARY OF THE INVENTION

In one aspect, the present invention provides compositions for modulating an immune response to a target antigen. Generally, these compositions comprise a lectin-interactive agent and an immune-modulating agent selected from an antigen that corresponds to at least a portion of the target antigen, an antigen-binding molecule that is immuno-interactive with the target antigen and an immune-modulating cell that modulates an immune response to the target antigen.

The target antigen is typically associated with a disease or condition of interest. In some embodiments, the target antigen is produced by a pathogenic organism or a cancer, which suitably expresses a lectin. In these embodiments, the composition is especially useful for stimulating or otherwise enhancing an immune response to the target antigen.

In other embodiments, the target antigen is associated with an unwanted immune response including, for example, transplant rejection, graft versus host disease, allergies, parasitic diseases, inflammatory diseases and autoimmune diseases. In these embodiments, the composition is especially useful for inducing a tolerogenic response including the induction of an anergic response, and the suppression of a future or existing immune response, to the target antigen.

The antigen that corresponds to at least a portion of the target antigen may be in soluble form (e.g., a peptide or polypeptide or a construct from which any one of these is expressible). Alternatively, the antigen may be a particle or cell (e.g., a virus, bacterium or whole cell) or presented by an antigen-presenting cell. (e.g., a professional or facultative antigen-presenting cell).

In certain embodiments, the antigen-presenting cell stimulates an immune response. In other embodiments, it induces a tolerogenic response. In still other embodiments, the antigen-presenting cell is a cell to which an immune response is required (e.g., tumour cell) and which has been optionally modified to enhance its antigen-presenting functions. In some embodiments of this type, the cell is modified by culturing the cell in the presence of a type II interferon (IN) and optionally at least one type I IFN for a time and under conditions sufficient to enhance the antigen-presenting function of the cell and washing the cell to remove the IFN. In other embodiments of this type, the cell is modified by introducing a construct into the cell from which one or more IFNs selected from a type II IFN and a type I IFN are expressible. In some embodiments, the antigen-presenting cell is an allogeneic antigen-presenting cell or cell line that shares major and/or minor histocompatability antigens to a recipient (also referred to herein as a 'generic' antigen-presenting cell or cell line).

Exemplary antigen-specific immune effector cells that may be used in concert with the lectin-interactive agent include antigen-specific T lymphocytes, including cytolytic T lymphocytes and helper T lymphocytes, T regulatory cells and B lymphocytes.

In embodiments in which the immune-modulating agent is an antigen-binding molecule, such a molecule will typically bind to or otherwise interact with the target antigen so as to reduce its level or functional activity.

Suitably, the lectin to which the agent binds is a galectin, which is especially selected from galectin-1, galectin-3 and galectin-9. In some embodiments, the lectin-interactive agent is a carbohydrate or carbohydrate-containing molecule including, but not restricted to: disaccharides non-limiting examples of which include, lactose, lactulose, lactosucrose, methyl β-lactoside, D-galactose, 4-O-β-D-galactopyranosyl-D-mannopyranoside, 3-O-β-D-galactopyranosyl-D-arabinose, 2'-O-methyllactose, lacto-N-biose, N-acetyllactosamine, and thiodigalactopyranoside; larger saccharides such as molecules comprising polylactosamine; as well as synthetic inhibitors such as thiodigalactoside and glycopolymers. Advantageously, the carbohydrate or carbohydrate containing molecule is non-metabolisable in the host to which the composition is administered. In certain embodiments, the lectin-interactive agent is selected from N-acetyl-lactosamine, β-lactosyl-thio-albumin, citrus pectin, D-lactitol monohydrate, lactobionic acid, benzyl 4-O-β-D-galactopyranosyl-β-D-glucopyranoside, methyl 4-O-β-D-galactopyranosyl-β-D-glucopyranoside, 2-methyl-β-D-galactose (1-4) D-glucose, carbomethoxyethylthioethyl 2 acetamido-2-deoxy-4-O-β-D galactopyranoyl-β-D-glucopyranoside, carboxyethylthioethyl 2 acetamido-2-deoxy 4-O-β-D galactopyranosyl-β-D-glucopyranoside-BSA conjugate, 4-nitrophenyl 2-acetamido-2-deoxy-3-O-β-D galactopyranosyl-β-D-glucopyranoside and N-propyl-β-lactoside.

In some embodiments, the composition further comprises one or more immunoregulatory molecules selected from co-stimulatory molecules (e.g., B7-1, B7-2, B7-3, ICAM-1 and ICAM-2), cytokines (interferons, granulocyte/macrophage-colony stimulating factor (GM-CSF), interleukin-10 and tumour necrosis factor α (TNF-α)) and co-inhibitory molecules (e.g., OX-2, programmed death-1 ligand (PD-1L)). Such molecules may be provided in soluble form. Alternatively, in cellular embodiments of the present invention, they may be produced intracellularly from a suitable expression construct or vector.

Another aspect of the present invention provides methods for modulating an immune response in a subject. These methods generally comprise administering to the subject a composition as broadly described above. The active components of the composition may be administered sequentially, separately or simultaneously. In certain embodiments, the immune response is a T-cell mediated response. Advantageously, these methods are useful for the treatment or prophylaxis of a disease or condition associated with the presence or aberrant expression of a target antigen in a subject. In certain embodiments, the disease or condition is treated or prevented by using a composition that stimulates or otherwise enhances an immune response to a target antigen. In these embodiments, the composition may comprise a soluble antigen that corresponds to at least a portion of the target antigen or an immune-stimulating cell (e.g., antigen-presenting cell or an immune effector cell such as an antigen-primed T lymphocyte or B lymphocyte) that stimulates an immune response to the target antigen. Suitably, the disease or condition is selected from a pathogenic infection, a disease characterised by immunodeficiency or a cancer.

In other embodiments, the disease or condition is treated or prevented by using a composition that elicits a tolerogenic response to a target antigen. In these embodiments, the composition may comprise an immune-attenuating cell (e.g., an antigen-presenting cell or T regulatory lymphocyte) that induces tolerance or otherwise attenuates an immune response to the target antigen. Suitably, the disease or condition is selected from transplant rejection, graft versus host disease, allergies, parasitic diseases, inflammatory diseases and autoimmune diseases.

In a further aspect, the invention contemplates the use of a lectin-interactive agent and an immune-modulating agent are broadly defined above in the manufacture of a medicament for modulating an immune response to a target antigen.

In still another aspect, the invention resides in the use of a lectin-interactive agent and an immune-modulating agent as broadly defined above in the manufacture of a medicament for treating or preventing a disease or condition associated with the presence or aberrant expression of a target antigen.

In another aspect, the invention provides methods for identifying a lectin-interactive agent as broadly described above. These methods generally comprise (a) culturing a first sample of a population of immune effector cells in the presence of a first sample of a lectin-expressing cell or pathogen; (b) culturing a second sample of the population in the presence of a second sample of the lectin-expressing cell or pathogen and a candidate agent suspected of having lectin-interaction activity, and (c) quantifying the immune effector cells in the first and second samples, respectively, whereby an increase in the number of immune effector cells in the second sample as compared to the first sample indicates that the candidate agent is a lectin-interactive agent.

In yet another aspect, the invention provides methods for assaying the activity of a lectin-interactive agent as broadly described above. These methods generally comprise (a) culturing a first sample of a population of immune effector cells in the presence of a first sample of a lectin-expressing cell or pathogen; (b) culturing a second sample of the population in the presence of a second sample of the lectin-expressing cell or pathogen and a lectin-interactive agent, and (c) quantifying the immune effector cells in the first and second samples, respectively. Typically, the higher the number of immune effector cells in the second sample as compared to the first sample, the higher the lectin-interactive activity (e.g., affinity) will be. In some embodiments, the population of immune effector cells is selected from populations of white blood cells, which can be homogenous or heterogeneous, illustrative examples of which include whole blood, fresh blood, or fractions thereof such as, but not limited to, peripheral blood mononuclear cells, buffy coat fractions of whole blood, packed red cells, irradiated blood, dendritic cells, monocytes, macrophages, neutrophils, lymphocytes, natural killer cells and natural killer T cells. In some embodiments, the lectin-expressing cell is a tumour cell (e.g., a melanoma cell or a breast cancer cell). In some embodiments, the immune effector cells are quantified using a cytolytic T lymphocyte assay.

DETAILED DESCRIPTION OF THE INVENTION

1. Definitions

Figure 1:
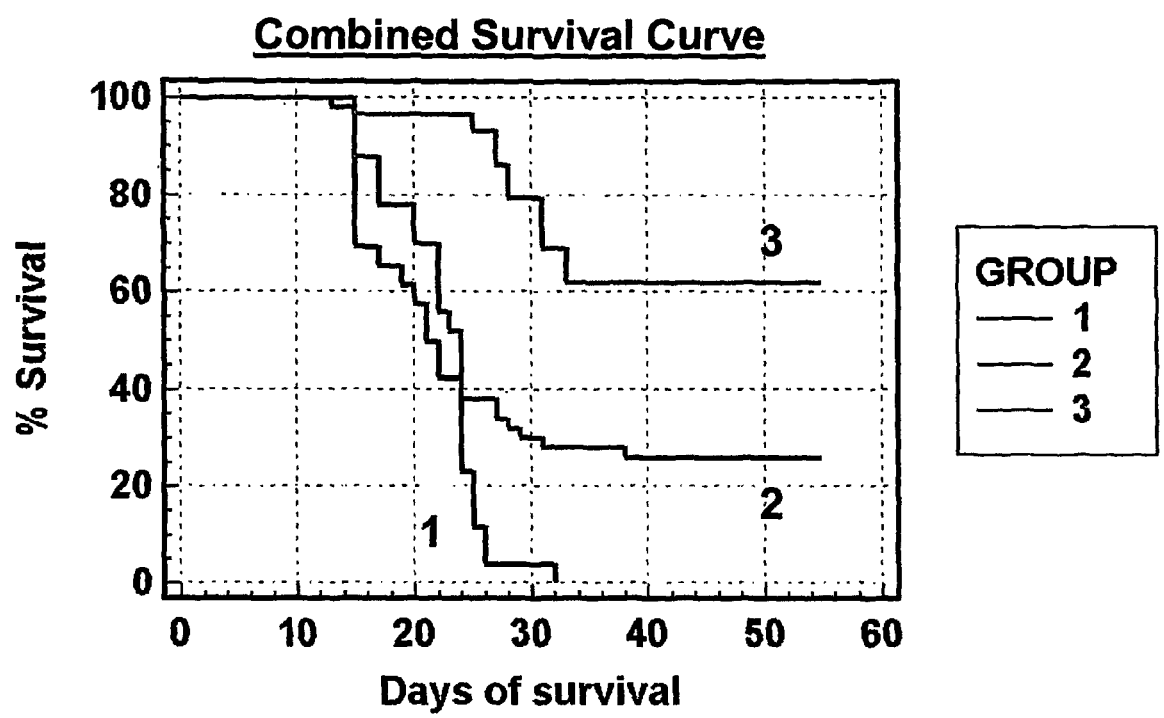
FIG. 1 is a graphical representation showing the effects of six weekly injections of (i) a vaccine comprising B16F10-B7.1high treated with IFN γ and IFN β in combination with addition of 20 mg/mL solution of lactulose at 1:1 ratio to the cell suspension (Group 3), or (ii) a vaccine comprising B16F10-B7.1high treated with IFN γ and IFN β alone (Group 2), or (iii) no vaccine (Group 1) on the survival of mice challenged with $5\times10^5$ live B16F10-B7.1med cells.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

The term "about" is used herein to refer to conditions (e.g., amounts, concentrations, time etc) that vary by as much as 30%, preferably by as much as 20%, and more preferably by as much as 10% to a specified condition.

The term "analogue" refers to a molecule that is substantially similar in function to a reference molecule or to a biologically active fragment thereof.

The term "anere" as used herein refers to a suppressed response, or a state of non-responsiveness, to a specified antigen or group of antigens by an immune system. For example, T lymphocytes and B lymphocytes are anergic when they cannot respond to their specific antigen under optimal conditions of stimulation.

By "antigen" is meant all, or part of, a protein, peptide, or other molecule or macromolecule capable of eliciting an immune response in a vertebrate animal, especially a mammal. Such antigens are also reactive with antibodies from animals immunised with that protein, peptide, or other molecule or macromolecule.

By "antigen-biniding molecule" is meant a molecule that has binding affinity for a target antigen. It will be understood that this term extends to immunoglobulins, immunoglobulin fragments and non-immunoglobulin derived protein frameworks that exhibit antigen-binding activity.

By "autologous" is meant something (e.g., cells, tissues etc) derived from the same organism.

The term "allogeneic" as used herein refers to cells, tissues, organisms etc that are of different genetic constitution.

By "biologically activefragient" is meant a fragment of a full-length parent polypeptide which fragment retains an activity of the parent polypeptide. As used herein, the term "biologically activefragient" includes deletion mutants and small peptides, for example of at least 6, 7, 8, 9, 10, 11, 12, 13, 14, 15, 16, 17, 18, 19, 20, 21, 22, 23, 24, 25, 26, 27, 28, 29 or 30 contiguous amino acids, which comprise an activity of the parent polypeptide. Peptides of this type may be obtained through the application of standard recombinant nucleic acid techniques or synthesised using conventional liquid or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of a polypeptide of the invention with proteinases such as endoLys-C, endoArg-C, endoGlu-C and *staphylococcus* V8-protease. The digested fragments can be purified by, for example, high performance liquid chromatographic (HPLC) techniques.

As used herein, a "cellular composition", "cellular vaccine" or "cellular immunogen" refers to a composition comprising at least one cell population, which is optionally inactivated, as an active ingredient.

As used herein, the term "cis-acting sequence" or "cis-regulatory region" or similar term shall be taken to mean any sequence of nucleotides which is derived from an expressible genetic sequence wherein the expression of the genetic sequence is regulated, at least in part, by the sequence of nucleotides. Those skilled in the art will be aware that a cis-regulatory region may be capable of activating, silencing, enhancing, repressing or otherwise altering the level of expression and/or cell-type-specificity and/or developmental specificity of any structural gene sequence.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

As used herein, "culturing", "culture" and the like refer to the set of procedures used in vitro where a population of cells (or a single cell) is incubated under conditions which have been shown to support the growth or maintenance of the cells in vitro. The art recognises a wide number of formats, media, temperature ranges, gas concentrations etc. which need to be defined in a culture system. The parameters will vary based on the format selected and the specific needs of the individual who practices the methods herein disclosed. However, it is recognised that the determination of culture parameters is routine in nature.

By "effective amount", in the context of modulating an immune response or treating or preventing a disease or condition, is meant the administration of that amount of composition to an individual in need thereof, either in a single dose or as part of a series, that is effective for that modulation, treatment or prevention. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

By "expression vector" is meant any autonomous genetic element capable of directing the synthesis of a protein encoded by the vector. Such expression vectors are known by practitioners in the art.

The term "gene" is used in its broadest context to include both a genomic DNA region corresponding to the gene as well as a cDNA sequence corresponding to exons or a recombinant molecule engineered to encode a functional form of a product.

By "derivative" is meant a polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions, or deletions that provide for functionally equivalent molecules.

To enhance immune response ("immunoenhancement"), as is well-known in the art, means to increase the animal's capacity to respond to foreign or disease-specific antigens (e.g., cancer antigens) i.e., those cells primed to attack such antigens are increased in number, activity, and ability to detect and destroy the those antigens. Strength of immune response is measured by standard tests including: direct measurement of peripheral blood lymphocytes by means known to the art; natural killer cell cytotoxicity assays (see, e.g., Provinciali M. et al. (1992, *J. Immunol. Meth.* 155: 19-24), cell proliferation assays (see, e.g., Vollenweider, I. And Groseurth, P. J. (1992, *J. Immunol. Meth.* 149: 133-135), immunoassays of immune cells and subsets (see, e.g., Loeffler, D. A., et al. (1992, *Cytom.* 13: 169-174); Rivoltini, L., et al. (1992, *Can. Immunol. Immunother.* 34: 241-251); or skin tests for cell-mediated immunity (see, e.g., Chang, A. E. et al. (1993, *Cancer Res.* 53: 1043-1050). Any statistically significant increase in strength of immune response as measured by the foregoing tests is considered "enhanced immune response""immunoenhancement" or "iiimnunopotentiation" as used herein. Enhanced immune response is also indicated by physical manifestations such as fever and inflammation, as well as healing of systemic and local infections, and reduction of symptoms in disease, i.e., decrease in tumour size, alleviation of symptoms of a disease or condition including, but not restricted to, leprosy, tuberculosis, malaria, naphthous ulcers, herpetic and papillomatous warts, gingivitis, artherosclerosis, the concomitants of AIDS such as Kaposi's sarcoma, bronchial infections, and the like. Such physical manifestations also define "enhanced immune response""immunoenhancement" or "immunopotentiation" as used herein.

By "greatly increased levels" or "high levels" in the context of molecular expression is meant expression of a molecule at levels that are 10-fold, more preferably 50-fold, more preferably 100-fold and more preferably 200-fold above a reference level. For example, B16High cells as used herein, express greatly increased levels of a B7 molecule on their surface, which levels are 10-fold, more preferably 50-fold, more preferably 100-fold and more preferably 200-fold above wild-type B16 cells.

Reference herein to "immunodeficient" includes reference to any condition in which there is a deficiency in the production of humoral and/or cell-mediated immunity.

Reference herein to "immuno-interactive" includes reference to any interaction, reaction, or other form of association between molecules and in particular where one of the molecules is, or mimics, a component of the immune system.

"Inactivation" of a cell is used herein to indicate that the cell has been rendered incapable of cell division to form progeny. The cell may nonetheless be capable of response to stimulus, or biosynthesis and/or secretion of cell products such as cytokines. Methods of inactivation are known in the art. Preferred methods of inactivation are treatment with toxins such as mitomycin C, or irradiation. Cells that have been fixed or permeabilised and are incapable of division are also examples of inactivated cells.

By "isolated" is meant material that is substantially or essentially free from components that normally accompany it in its native state.

A composition is "immunogenic" if it is capable of either: a) generating an immune response against an antigen (e.g., a tumour antigen) in a naive individual; or b) reconstituting, boosting, or maintaining an immune response in an individual beyond what would occur if the compound or composition was not administered. A composition is immunogenic if it is capable of attaining either of these criteria when administered in single or multiple doses.

By "modulating" is meant increasing or decreasing, either directly or indirectly, the level and/or functional activity of a target molecule. For example, an agent may indirectly modulate the said level/activity by interacting with a molecule other than the target molecule. In this regard, indirect modulation of a gene encoding a target polypeptide includes within its scope modulation of the expression of a first nucleic acid molecule, wherein an expression product of the first nucleic acid molecule modulates the expression of a nucleic acid molecule encoding the target polypeptide. In certain embodiments, "modulation" or "modulating" means that a desired/selected response is more efficient (e.g., at least 10%, 20%, 30%, 40%, 50%, 60% or more), more rapid (e.g., at least 10%, 20%, 30%, 40%, 50%, 60% or more), greater in magnitude (e.g., at least 10%, 20%, 30%, 40%, 50%, 60% or more), and/or more easily induced (e.g., at least 10%, 20%, 30%, 40%, 50%, 60% or more) than if the antigen had been used alone.

The term "5' non-coding region" is used herein in its broadest context to include all nucleotide sequences which are derived from the upstream region of an expressible gene, other than those sequences which encode amino acid residues which comprise the polypeptide product of said gene, wherein 5' non-coding region confers or activates or otherwise facilitates, at least in part, expression of the gene.

By "non-metabolisable," "not metabolised" and the like is meant a lectin-interactive agent that is not converted in a living organism (e.g., by catabolism or anabolism) to an agent that is incapable of interacting with the lectin.

By "obtained from" is meant that a sample such as, for example, a nucleic acid extract or polypeptide extract is isolated from, or derived from, a particular source of the host. For example, the extract may be obtained from a tissue or a biological fluid isolated directly from the host.

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotides and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule may vary depending on the particular application. An oligonucleotide is typically rather short in length, generally from about 10 to 30 nucleotides, but the term can refer to molecules of any length, although the term "polynucleotide" or "nucleic acid" is typically used for large oligonucleotides.

The term "operably connected" or "operably linked" as used herein means placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e., the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

The terms "patient," "subject," "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates, rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc), marine mammals (e.g., dolphins, whales), reptiles (snakes, frogs, lizards etc), and fish. A preferred subject is a human in need of treatment or prophylaxis for a condition or disease, which is associated with the presence or aberrant expression of an antigen of interest. However, it will be understood that the aforementioned terms do not imply that symptoms are present.

By "pharmaceutically-acceptable carrier" is meant a solid or liquid filler, diluent or encapsulating substance that may be safely used in topical or systemic administration.

The term "pharmaceutically compatible salt" as used herein refers to a salt which is toxicologically safe for human and animal administration. This salt may be selected from a group including hydrochlorides, hydrobromides, hydroiodides, sulphates, bisulphates, nitrates, citrates, tartrates, bitartrates, phosphates, malates, maleates, napsylates, fumarates, succinates, acetates, terephthalates, pamoates and pectinates.

The term "polynucleotide" or "nucleic acid" as used herein designates mRNA, RNA, cRNA, cDNA or DNA. The term typically refers to oligonucleotides greater than 30 nucleotides in length.

The terms "polynucleotide variant" and "variant" refer to polynucleotides displaying substantial sequence identity with a reference polynucleotide sequence or polynucleotides that hybridise with a reference sequence under stringent conditions that are defined hereinafter. These terms also encompasses polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. The terms "polynucleotide variant" and "variant" also include naturally occurring allelic variants.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

The term "polypeptide variant" refers to polypeptides which vary from a reference polypeptide by the addition, deletion or substitution of at least one amino acid. It is well understood in the art that some amino acids may be changed to others with broadly similar properties without changing the nature of the activity of the polypeptide. Accordingly, polypeptide variants as used herein encompass polypeptides that have similar activities to a parent polypeptide selected from an interferon α, an interferon β, an interferon γ, a B7-1 molecule and a B7-2 molecule. Preferred variant polypeptides comprise conservative amino acid substitutions. Exemplary conservative substitutions in a polypeptide may be made according to the following table:

TABLE A

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Substantial changes in function are made by selecting substitutions that are less conservative than those shown in TABLE A. Other replacements would be non-conservative substitutions and relatively fewer of these may be tolerated. Generally, the substitutions which are likely to produce the greatest changes in a polypeptide's properties are those in which (a) a hydrophilic residue (e.g., Ser or Asn) is substituted for, or by, a hydrophobic residue (e.g., Ala, Leu, Ile, Phe or Val); (b) a cysteine or proline is substituted for, or by, any other residue; (c) a residue having an electropositive side chain (e.g., Arg, H is or Lys) is substituted for, or by, an electronegative residue (e.g., Glu or Asp) or (d) a residue having a smaller side chain (e.g., Ala, Ser) or no side chain (e.g., Gly) is substituted for, or by, one having a bulky side chain (e.g., Phe or Trp).

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e., upstream activating sequences, enhancers and silencers) which alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene. Preferred promoters according to the invention may contain additional copies of one or more specific regulatory elements to further enhance expression in a cell, and/or to alter the timing of expression of a structural gene to which it is operably connected.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

As used herein "stimulating" an immune or immunological response refers to administration of a composition that initiates, boosts, or maintains the capacity for the host's immune system to react to a target substance, such as a foreign molecule, an allogeneic cell, or a tumour cell, at a level higher than would otherwise occur. Stimulating a "primary" immune response refers herein to eliciting specific immune reactivity in a subject in which previous reactivity was not detected; for example, due to lack of exposure to the target antigen, refractoriness to the target, or immune suppression. Stimulating a "secondary" response refers to the reinitiation, boosting, or maintenance of reactivity in a subject in which previous reactivity was detected; for example, due to natural immunity, spontaneous immunisation, or treatment using one or several compositions or procedures.

The term "treatment," "treat," "treated" and the like is meant to include both therapeutic and prophylacetic treatment.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

2. Compositions

The present invention stems at least in part from the discovery that a subject's immune response to an antigen is enhanced by the introduction of a lectin-interactive agent. Not wishing to be bound by any one particular theory or mode of operation, it is proposed that the lectin-interactive agent acts as an adjuvant by competing with glycoprotein receptors on the surface of T cells for binding to lectins, which inhibits lectin-induced glycoprotein receptor clustering and prevents or attenuates the inhibition of T cell activation. This results in the prolongation of T cell activation and the concomitant enhanced duration of immunity or tolerance to an antigen of interest. Accordingly, the present invention provides in one aspect compositions for modulating an immune response to a target antigen, wherein the compositions generally comprise a lectin-interactive agent and an immune-modulating agent selected from an antigen that corresponds to at least a portion of the target antigen, an antigen-binding molecule that is immuno-interactive with the target antigen and an immune-modulating cell that modulates an immune response to the target antigen.

2.1 Lectin-Interactive Agents

The lectin-interactive agent includes any molecule or compound that directly or indirectly binds or physically associates with a lectin and that suitably blocks, inhibits or otherwise antagonises at least one of its functions or activities (e.g., binding to or interaction with one or more surface molecules present on white blood cells, especially lymphocytes and more especially T lymphocytes). The binding or association may involve the formation of an induced magnetic field or paramagnetic field, covalent bond formation, an ionic interaction such as, for example, occur in an ionic lattice, a hydrogen bond or alternatively, a van der Waals interaction such as, for example, a dipole-dipole interaction, dipole-induced-dipole interaction, induced-pole-induced-dipole interaction or a repulsive interaction or any combination of the above forces of attraction. In certain embodiments, the lectin is a galectin, which is suitably selected from galectin-1, galectin-3 and galectin-9. The lectin is suitably expressed by an organism, illustrative examples of which include bacteria, entamoeba, protozoans (e.g., malaria), insects, gastropods, plants or animals. In certain embodiments, the lectin is an animal lectin which is suitably selected from the group including, but not limited to calnexin, M-type lectins, L-lectins, P-lectins, C-lectins, galactoside-binding lectins, I-type lectins or R-lectins. Desirably, the lectin is galectin which is especially selected from galectin-1, galectin-3 and galectin-9.

The lectin-interactive agent is typically selected from the group consisting of polynucleotides, polypeptides, antibodies, lipids or carbohydrates. In certain advantageous embodiments, the lectin-interactive agent is in soluble form.

In some embodiments, the lectin-interactive agent is a carbohydrate or carbohydrate-containing molecule (e.g., glycoproteins) illustrative examples of which include: monosaccharide, disaccharides (e.g., lactose, lactulose, lactosucrose, methyl 4-lactoside, D-galactose, 4-O-β-D-galactopyranosyl-D-mannopyranoside, 3-O-β-D-galactopyranosyl-D-arabinose, 2'-O-methyllactose, lacto-N-biose, N-acetyllactosamine, and thiodigalactopyranoside); larger saccharides (e.g., polylactosamine, polylactosamine-carrying glycopeptides, modified plant pectin polysaccharide); as well as synthetic inhibitors (e.g., thiodigalactoside), glycopeptides especially those containing lactose or galactose (Glinsky et al., 1996, *Cancer Research* 56:5319-5324; Naidenko et al. 2000, *Glycobiology* 10:abstract 60), N-acetyllactosamine derivatives such as those described in International Publication WO 02/057284, modified polysaccharides disclosed in U.S. Patent Application Publication Nos. 2002/0107222 and 2003/0013681, starburst dendrimers (Andre et al. 1999, *Glycobiology* 11: 1253-1262) and glycopolymers (Pohl et al., 1999, *Synthesis* 1515-1519). In certain embodiments, the carbohydrate or carbohydrate-containing molecule is not metabolised in the host to which the composition is administered. Illustrative examples of this type include lactulose, methyl 2-acetamido-2-deoxy-4-O-(3-[3-carboxypropanamido]-3-deoxy-β-D-galactopyranosyl)-β-D-glucopyranoside, methyl 2-acetamido-2-deoxy-4-O-(3-[{Z}-3-carboxypropenamido]-3-deoxy-β-D-galactopyranosyl)-β-D-glucopyranoside, methyl 2-acetamido-2-deoxy-4-O-(3-benzamido-3-deoxy-β-D-galactopyranosyl)-β-D-glucopyranoside, methyl 2-acetamido-2-deoxy-4-O-(3-[2-carboxybenzamido]-3-deoxy-β-D-galactopyranosyl)-β-D-glucopyranoside, methyl 2-acetamido-2-deoxy-4-O-[4-methoxy-2,3,5,6-tetrafluorobenzamido]-3-deoxy-β-D-galactopyranosyl)-β-D-glucopyranoside, methyl 2-acetamido-2-deoxy-4-O-3-[2-carboxy-3,4,5,6-tetrafluoro-benzamido]-3-deoxy-β-D-galactopyranosyl)-β-D-glucopyranoside, methyl 2-acetamido-2-deoxy-4-O-(3-methane-sulfonamido-3-deoxy-β-D-galactopyranosyl)-β-D-glucopyranoside, methyl 2-acetamido-2-deoxy-4-O-(3-[4-nitrobenzenesulfonamido]-3-deoxy-β-D-galactopyranosyl)-β-D-glucopyranoside, methyl 2-acetamido-2-deoxy-4-O-3-phenylaminocarbonylamino-3-deoxy-β-D-galactopyranosyl)-β-D-glucopyranoside, methyl 2-acetamido2-deoxy-4-O-(2-aminoacetamido-3-deoxy-β-D-galactopyranosyl)-β-D-glueopyranoside, methyl 2-acetamido2-deoxy-4-O-3-[{2S}-2-amino-3-carboxy-propanamido)-3-deoxy-β-D-galactopyranosyl)-β-D-glucopyranoside. Suitably, the lectin-interactive agent is lactulose or synthetic or semi-synthetic analogue thereof.

Other illustrative examples of carbohydrates include those described in United States Patent Application Publication No. 20040147730. Representative carbohydrates of this type include, but are not limited to, methyl 2-acetamido-2-deoxy-4-O-3-[3-carboxypropanamido]-3-deoxy-β-D-galactopyranosyl)-β-D-glucopyranoside, methyl 2-acetamido-2-deoxy-4-O-(3-[{Z}-3-carboxypropenamido]-3-deoxy-β-D-galactopyranosyl)-β-D-glucopyranoside, methyl 2-acetamido-2-deoxy-4-O-(3-benzamido-3-deoxy-β-D-galactopyranosyl)-β-D-glucopyranoside, methyl 2-acetamido-2-deoxy-4-O-(3-[2-carboxybenzamido]-3-deoxy-β-D-galactopyranosyl)-β-D-glucopyranoside, methyl 2-acetamido-2-deoxy-4-O-(3-[4-methoxy-2,3,5,6-tetrafluorobenzamido]-3-deoxy-β-D-galactopyranosyl)-β-D-glucopyranoside, methyl 2-acetamido-2-deoxy-4-O-(3-(2-carboxy-3,4,5,6-tetrafluorobenzamido]-3-deoxy-β-D-galactopyranosyl)-β-D-glucopyranoside, methyl 2-acetamido-2-deoxy-4-O-(3-methane-sulfonamido-3-deoxy-β-D-galactopyranosyl)-β-D-glucopyranoside, methyl 2-acetamido-2-deoxy-4-O-(3-[4-nitrobenzenesulfonamido]-3-deoxy-β-D-galactopyranosyl)-β-D-glucopyranoside, methyl 2-acetamido-2-deoxy-4-O-(3-phenylaminocarbonylamino-3-deoxy-β-D-galactopyranosyl)-β-D-glucopyranoside, methyl 2-acetamido-2-deoxy-4-O-(2-aminoacetamido-3-deoxy-β-D-galactopyranosyl)-β-D-glucopyranoside, methyl 2-acetamido-2-deoxy-4-O-(3-[{2S}-2-amino-3-carboxy-propanamido]-3-deoxy-β-D-galactopyranosyl)-β-D-glucopyranoside. In some embodiments of this type, the carbohydrate is methyl 2-acetamido-2-deoxy-40-(3-benzamido-3-deoxy-β-D-galactopyranosyl)-β-D-glucopyranoside, methyl 2-acetamido-2-deoxy-4-O-(3-[2-carboxy-benzamido]-3-deoxy-β-D-galactopyranosyl)-β-D-glucopyranoside, methyl 2-acetamido-2-deoxy-4-O-(3-[4-methoxy-2,3,5,6-tetrafluorobenzamido]-3-deoxy-β-D-galactopyranosyl)-β-D-glucopyranoside, or methyl 2-acetamido-2-deoxy-4-O-(3-[2-carboxy-3,4,5,6-tetrafluorobenzamido]-3-deoxy-β-D-galactopyranosyl)-D-glucopyranoside.

The lectin-interactive agents will usually have a binding affinity for the lectin in the range from about $10^{-3}$ to about $10^{-9}$ M, typically from about $10^{-5}$ to about $10^{-8}$ M, and more typically from about $10^{-4}$ to about $10^{-7}$M.

In certain advantageous embodiments, a plurality of carbohydrate lectin-interactive agents, as described for example above, are used in the compositions of the invention (e.g., at least 2, 3, 4, 5 and in some cases 6, 7, 8 or more such agents). In illustrative examples of this type, one of the carbohydrates is a soluble disaccharide that can diffuse readily through an animal body (e.g., to provide long range protection to immune cells from the negative effects of lectins) and the other carbohydrate is a larger saccharide (e.g., a polylactosamine such as a Citrus pectin) that is partially soluble to thereby limit its diffusion from the site of delivery (e.g., the site of a tumour).

Desirably, the lectin-interactive agents are non-toxic to the host with minimal or negligible side effects.

2.2 Immune-Modulating Agents 2.2.1 Antigens

The present invention contemplates the use in the compositions of the invention of any antigen that corresponds to at least a portion of a target antigen of interest for stimulating an immune response to the target antigen. Such an antigen may be in soluble form (e.g., peptide, polypeptide or a nucleic acid molecule from which a peptide or polypeptide is expressible) or in the form of whole cells or attenuated pathogen preparations (e.g., attenuated virus or bacteria) or it may be presented by antigen-presenting cells as described in more detail below.

Target antigens useful in the present invention can be any type of biological molecule including, for example, simple intermediary metabolites, sugars, lipids, and hormones as well as macromolecules such as complex carbohydrates, phospholipids, nucleic acids, polypeptides and peptides. Target antigens may be selected from endogenous antigens produced by a host or exogenous antigens that are foreign to the host. Suitable endogenous antigens include, but are not restricted to, self-antigens that are targets of autoimmune responses as well as cancer or tumour antigens. Illustrative examples of self antigens useful in the treatment or prevention of autoimmune disorders include, but not limited to, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia greata, allergic responses due to arthropod bite reactions, Crohn's disease, ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing haemorrhagic encephalopathy, idiopathic bilateral progressive sensorineural hearing loss, aplastic anaemia, pure red cell anaemia, idiopathic thrombocytopenia, polychondritis, Wegener's granulomatosis, chronic active hepatitis, Stevens-Johnson syndrome, idiopathic sprue, lichen planus, Graves opthalmopathy, sarcoidosis, primary biliary cirrhosis, uveitis posterior, and interstitial lung fibrosis. Other autoantigens include those derived from nucleosomes for the treatment of systemic lupus erythematosus (e.g., GenBank Accession No. D28394; Bruggen et al., 1996, *Ann. Med. Interne* (Paris), 147:485-489) and from the 44,000 Da peptide component of ocular tissue cross-reactive with *O. volvulus* antigen (McKeclmie et al., 1993, *Ann Trop. Med. Parasitol.* 87:649-652). Thus, illustrative autoantigens antigens that can be used in the compositions and methods of the present invention include, but are not limited to, at least a portion of a lupus autoantigen, Smith, Ro, La, U1-RNP, fibrillin (scleroderma), pancreatic β cell antigens, GAD65 (diabetes related), insulin, myelin basic protein, myelin proteolipid protein, histones, PLP, collagen, glucose-6-phosphate isomerase, citrullinated proteins and peptides, thyroid antigens, thyroglobulin, thyroid-stimulating hormone (TSH) receptor, various tRNA synthetases, components of the acetyl choline receptor (AchR), MOG, proteinase-3, myeloperoxidase, epidermal cadherin, acetyl choline receptor, platelet antigens, nucleic acids, nucleic acid:protein complexes, joint antigens, antigens of the nervous system, salivary gland proteins, skin antigens, kidney antigens, heart antigens, lung antigens, eye antigens, erythrocyte antigens, liver antigens and stomach antigens.

Non-limiting examples of cancer or tumour antigens include antigens from a cancer or tumour selected from ABL1 protooncogene, AIDS related cancers, acoustic neuroma, acute lymphocytic leukaemia, acute myeloid leukaemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumours, breast cancer, CNS tumours, carcinoid tumours, cervical cancer, childhood brain tumours, childhood cancer, childhood leukaemia, childhood soft tissue sarcoma, chondrosarcoma, choriocarcinoma, chronic lymphocytic leukaemia, chronic myeloid leukaemia, colorectal cancers, cutaneous t-cell lymphoma, dermatofibrosarcoma-protuberans, desmoplastic-small-round-cell-tumour, ductal carcinoma, endocrine cancers, endometrial cancer, ependymoma, oesophageal cancer, Ewing's Sarcoma, Extra-Hepatic Bile Duct Cancer, Eye Cancer, Eye: Melanoma, Retinoblastoma, Fallopian Tube cancer, Fanconi anaemia, fibrosarcoma, gall bladder cancer, gastric cancer, gastrointestinal cancers, gastrointestinal-carcinoid-tumour, genitourinary cancers, germ cell tumours, gestational-trophoblastic-disease, glioma, gynaecological cancers, haematological malignancies, hairy cell leukaemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukaemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumour-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nepbroblastoma, neuroblastoma, neurofibromatosis, Nijmegen breakage syndrome, non-melanoma skin cancer, non-small-cell-lung-cancer (NSCLC), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumours, pituitary cancer, polycythemia vera, prostate cancer, rare-cancers-and-associated-disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumours, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/–ureter), trophoblastic cancer, urethral cancer, urinary system cancer, uroplakins, uterine sarcoma, uterus cancer, vaginal cancer, vulva cancer, Waldenstrom's-Macroglobulinemia, Wilms' Tumour. In certain embodiments, the cancer or tumour relates to melanoma. Illustrative examples of melanoma-related antigens include melanocyte differentiation antigen (e.g., gp100, MART, Melan-A/MART-1, TRP-1, Tyros, TRP2, MC1R, MUC1F, MUC1R or a combination thereof) and melanoma-specific antigens (e.g., BAGE, GAGE-1, gp100In4, MAGE-1 (e.g., GenBank Accession No. X54156 and AA494311), MAGE-3, MAGE4, PRAME, TRP2IN2, NYNSO1a, NYNSO1b, LAGE1, p97 melanoma antigen (e.g., GenBank Accession No. M12154) p5 protein, gp75, oncofetal antigen, GM2 and GD2 gangliosides, cdc27, p21ras, gp100$^{Pmel117}$ or a combination thereof. Other tumour-specific antigens include, but are not limited to: etv6, aml1, cyclophilin b (acute lymphoblastic leukemia); Ig-idiotype (B cell lymphoma); E-cadherin, α-catenin, β-catenin, γ-catenin, p1120ctn (glioma); p21ras (bladder cancer); p21ras (biliary cancer); MUC family, HER2/neu, c-erbB-2 (breast cancer); p53, p21ras (cervical carcinoma); p21ras, HER2/neu, c-erbB-2, MUC family, Cripto-1protein, Pim-1 protein (colon carcinoma); Colorectal associated antigen (CRC)—CO17-1A/GA733, APC (colorectal cancer); carcinoembryonic antigen (CEA) (colorectal cancer; choriocarcinoma); cyclophilin b (epithelial cell cancer); HER2/neu, c-erbB-2, ga733 glycoprotein (gastric cancer); α-fetoprotein (hepatocellular cancer); Imp-1, EBNA-1 (Hodgkin's lymphoma); CEA, MAGE-3, NY-ESO-1 (lung cancer); cyclophilin b (lymphoid cell-derived leukemia); MUC family, p21ras (myeloma); HER2/neu, c-erbB-2 (non-small cell lung carcinoma); Imp-1, EBNA-1 (nasopharyngeal cancer); MUC family, HER2/neu, c-erbB-2, MAGE-A4, NY-ESO-1 (ovarian cancer); Prostate Specific Antigen (PSA) and its antigenic epitopes PSA-1, PSA-2, and PSA-3, PSMA, HER2/neu, c-erbB-2, ga733 glycoprotein (prostate cancer); HER2/neu, c-erbB-2 (renal cancer); viral products such as human papilloma virus proteins (squamous cell cancers of the cervix and oesophagus); NY-ESO-1 (testicular cancer); and HTLV-1 epitopes (C cell leukemia).

Foreign antigens are suitably selected from transplantation antigens, allergens as well as antigens from pathogenic organisms. Transplantation antigens can be derived from donor cells or tissues from e.g., heart, lung, liver, pancreas, kidney, neural graft components, or from the donor antigen-presenting cells bearing MHC loaded with self antigen in the absence of exogenous antigen.

Non-limiting examples of allergens include Fel d 1 (i.e., the feline skin and salivary gland allergen of the domestic cat *Felis domesticus*, the amino acid sequence of which is disclosed International Publication WO 91/06571), Der p L Der p II, Der fi or Der fi (i.e., the major protein allergens from the house dust mite *dermatophagoides*, the amino acid sequence of which is disclosed in International Publication WO 94/24281). Other allergens may be derived, for example from the following: grass, tree and weed (including ragweed) pollens; fungi and moulds; foods such as fish, shellfish, crab, lobster, peanuts, nuts, wheat gluten, eggs and milk; stinging insects such as bee, wasp, and hornet and the chimomidae (non-biting midges); other insects such as the housefly, fruitfly, sheep blow fly, screw worm fly, grain weevil, silkworm, honeybee, non-biting midge larvae, bee moth larvae, mealworm, cockroach and larvae of *Tenibrio molitor* beetle; spiders and mites, including the house dust mite; allergens found in the dander, urine, saliva, blood or other bodily fluid of mammals such as cat, dog, cow, pig, sheep, horse, rabbit, rat, guinea pig, mouse and gerbil; airborne particulates in general; latex; and protein detergent additives.

Exemplary pathogenic organisms include, but are not limited to, viruses, bacteria, fungi parasites, algae and protozoa and amoebae. Illustrative examples of viruses include viruses responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Epstein-Barr virus and other herpesviruses such as papillomavirus, Ebola virus, influenza virus, Japanese encephalitis (e.g., GenBank Accession No. E07883), dengue (e.g., GenBank Accession No. M24444), hantavirus, Sendai virus, respiratory syncytial virus, othromyxoviruses, vesicular stomatitis virus, visna virus, cytomegalovirus and human immunodeficiency virus (HIV) (e.g., GenBank Accession No. U18552). Any suitable antigen derived from such viruses are useful in the practice of the present invention. For example, illustrative retroviral antigens derived from HIV include, but are not limited to, antigens such as gene products of the gag, pol, and env genes, the Nef protein, reverse transcriptase, and other HIV components. Illustrative examples of hepatitis viral antigens include, but are not limited to, antigens such as the S, M, and L proteins of hepatitis B virus, the pre-S antigen of hepatitis B virus, and other hepatitis, e.g., hepatitis A, B, and C, viral components such as hepatitis C viral RNA. Illustrative examples of influenza viral antigens include; but are not limited to, antigens such as hemagglutinin and neuramimidase and other influenza viral components. Illustrative examples of measles viral antigens include, but are not limited to, antigens such as the measles virus fusion protein and other measles virus components. Illustrative examples of rubella viral antigens include, but are not limited to, antigens such as proteins E1 and E2 and other rubella virus components; rotaviral antigens such as VP7sc and other rotaviral components. Illustrative examples of cytomegaloviral antigens include, but are not limited to, antigens such as envelope glycoprotein B and other cytomegaloviral antigen components. Non-limiting examples of respiratory syncytial viral antigens include antigens such as the RSV fusion protein, the M2 protein and other respiratory syncytial viral antigen components. Illustrative examples of herpes simplex viral antigens include, but are not limited to, antigens such as immediate early proteins, glycoprotein D, and other herpes simplex viral antigen components. Non-limiting examples of varicella zoster viral antigens include antigens such as 9PI, gpII, and other varicella zoster viral antigen components. Non-limiting examples of Japanese encephalitis viral antigens include antigens such as proteins E, M-E, M-E-NS 1, NS 1, NS 1-NS2A, 80% E, and other Japanese encephalitis viral antigen components. Representative examples of rabies viral antigens include, but are not limited to, antigens such as rabies glycoprotein, rabies nucleoprotein and other rabies viral antigen components. Illustrative examples of papillomavirus antigens include, but are not limited to, the L1 and L2 capsid proteins as well as the E6/E7 antigens associated with cervical cancers, See Fundamental Virology, Second Edition, eds. Fields, B. N. and Knipe, D. M., 1991, Raven Press, New York, for additional examples of viral antigens.

Illustrative examples of fungi include *Acremoniuin* spp., *Aspergillus* spp., *Basidiobolus* spp., *Bipolaris* spp., *Blastomyces derinatidis*, *Candida* spp., *Cladophialophora carrionii*, *Coccoidiodes immitis*, *Conidiobolus* spp., *Cryptococcus* spp., *Curvularia* spp., *Epidermophytoni* spp., *Exophiala jeanselmei*, *Exserohilunm* spp., *Fonsecaea compacta*, *Fonsecaea pedrosoi*, *Fusarium oxsporum*, *Fusarium solani*, *Geotrichum candidum*, *Histoplasma capsulatum* var. *capsulatum*, *Histoplasma capsulatum* var. *duboisii*, *Hortaea werneckii*, *Lacazia loboi*, *Lasiodiplodia theobromae*, *Leptosphaeria senegalenisis*, *Madurella grisea*, *Madurella mycetomatis*, *Malassezia furfur*, *Microsporum* spp., *Neotestudina rosatii*, *Onychocola canadensis*, *Paracoccidioides brasiliensis*, *Phialophora verrucosa*, *Piedraia hortae*, *Piedra iahortae*, *Pityriasis versicolor*, *Pseudallesheria boydii*, *Pyrenochaeta romeroi*, *Rhizopus arrhizus*, *Scopulariopsis brevicaulis*, *Scytalidium dimidiatum*, *Sporothrix schenckii*, *Trichophyton* spp., *Trichosporon* spp., *Zygomcete fungi*, *Absidia coryinbifera*, *Rhizomucor pusillus* and *Rhizopus arrhizus*. Thus, illustrative fungal antigens that can be used in the compositions and methods of the present invention include, but are not limited to, candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Illustrative examples of bacteria include bacteria that are responsible for diseases including, but not restricted to, diphtheria (e.g., *Corynebacterium diphtheria*), pertussis (e.g., *Bordetella pertussis*, GenBank Accession No. M35274), tetanus (e.g., *Clostridium tetani*, GenBank Accession No. M64353), tuberculosis (e.g., *Mycobacterium tuberculosis*), bacterial pneumonias (e.g., *Haemophilus influenzae*.), cholera (e.g., *Vibrio cholerae*), anthrax (e.g., *Bacillus antliracis*), typhoid, plague, shigellosis (e.g., *Shigella dysenteriae*), botulism (e.g., *Clostridium botulinum*), salmonellosis (e.g., GenBank Accession No. L03833), peptic ulcers (e.g., *Helicobacter pylori*), Legionnaire's Disease, Lyme disease (e.g., GenBank Accession No. U59487), Other pathogenic bacteria include *Escherichia coli*, *Clostridium perfringens*, *Pseudomonas aeruginosa*, *Staphylococcus aureus* and *Streptococcus pyogenes*. Thus, bacterial antigens which can be used in the compositions and methods of the invention include, but are not limited to: pertussis bacterial antigens such as pertussis toxin, filamentous hemagglutinin, pertactin, F M2, FIM3, adenylate cyclase and other pertussis bacterial antigen components; diphtheria bacterial antigens such as diphtheria toxin or toxoid and other diphtheria bacterial antigen components; tetanus bacterial antigens such as tetanus toxin or toxoid and other tetanus bacterial antigen components, streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components, pneumococcal bacterial antigens such as pneumolysin, pneumococcal capsular polysaccharides and other pnermiococcal bacterial antigen components; *Haemophilus influenza* bacterial antigens such as capsular polysaccharides and other *Haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

Illustrative examples of protozoa include protozoa that are responsible for diseases including, but not limited to, malaria (e.g., GenBank Accession No. X53832), hookworm, onchocerciasis (e.g., GenBank Accession No. M27807), schistosomiasis (e.g., GenBank Accession No. LOS 198), toxoplasmosis, trypanosomiasis, leishmaniasis, giardiasis (GenBank Accession No. M33641), amoebiasis, filariasis (e.g., GenBank Accession No. J03266), borreliosis, and trichinosis. Thus, protozoal antigens which can be used in the compositions and methods of the invention include, but are not limited to: *plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; *toxoplasma* antigens such as SAG-1, p30 and other toxoplasmal antigen components; schistosomae antigens such as glutathione-S-transferase, paramyosin, and other schistosomal antigen components; *leishmania major* and other leishmaniae antigens such as gp63, lipophosphoglycan and its associated protein and other leishmanial antigen components; and trypanosoma cruzi antigens such as the 75-77 kDa antigen, the 56 kDa antigen and other trypanosomal antigen components.

The present invention also contemplates toxin components as antigens. Illustrative examples of toxins include, but are not restricted to, staphylococcal enterotoxins, toxic shock syndrome toxin; retroviral antigens (e.g., antigens derived from HIV), streptococcal antigens, staphylococcal enterotoxin-A (SEA), staphylococcal enterotoxin-B (SEB), staphylococcal enterotoxin$_{1-3}$ (SEF$_{1-3}$), staphylococcal enterotoxin-D (SED), staphylococcal enterotoxin-E (SEE) as well as toxins derived from mycoplasma, mycobacterium, and herpes viruses.

The antigen corresponding to at least a portion of the target antigen may be isolated from a natural source or may be prepared by recombinant techniques as known in the art. For example, peptide antigens can be eluted from the MHC and other presenting molecules of antigen-presenting cells obtained from a cell population or tissue for which a modified immune response is desired. The eluted peptides can be purified using standard protein purification techniques known in the art (Rawson et al., 2000, Cancer Res 60(16), 4493-4498. If desired, the purified peptides can be sequenced and synthetic versions of the peptides produced using standard protein synthesis techniques as for example described below. Alternatively, crude antigen preparations can be produced by isolating a sample of a cell population or tissue for which a modified immune response is desired, and either lysing the sample or subjecting the sample to conditions that will lead to the formation of apoptotic cells (e.g., irradiation with ultra violet or with γ rays, viral infection, cytokines or by depriving cells of nutrients in the cell culture medium, incubation with hydrogen peroxide, or with drugs such as dexamethasone, ceramide chemotherapeutics and anti-hormonal agents such as Lupron or Tamoxifen). The lysate or the apoptotic cells can then be used as a source of crude antigen for use in soluble form or for contact with antigen-presenting cells as described in more detail below.

When the antigen is known, it may be conveniently prepared in recombinant form using standard protocols as for example described in: Sambrook, et al., MOLECULAR CLONING. A LABORATORY MANUAL (Cold Spring Harbor Press, 1989), in particular Sections 16 and 17; Ausubel et al., CURRENT PROTOCOLS IN MOLECULAR BIOLOGY (John Wiley & Sons, Inc. 1994-1998), in particular Chapters 10 and 16; and Coligan et al., CURRENT PROTOCOLS IN PROTEIN SCIENCE (John Wiley & Sons, Inc. 1995-1997), in particular Chapters 1, 5 and 6. Typically, an antigen may be prepared by a procedure including the steps of (a) providing an expression vector from which the target antigen or analogue or mimetic thereof is expressible; (b) introducing the vector into a suitable host cell; (c) culturing the host cell to express recombinant polypeptide from the vector; and (d) isolating the recombinant polypeptide.

In general, the expression vector will comprise an antigen-encoding polynucleotide which is operably connected to a regulatory polynucleotide. The antigen-encoding polynucleotide can be constructed from any suitable parent polynucleotide that codes for an antigen that corresponds to the target antigen of interest. The parent polynucleotide is suitably a natural gene or portion thereof. However, it is possible that the parent polynucleotide is not naturally-occurring but has been engineered using recombinant techniques. The regulatory polynucleotide suitably comprises transcriptional and/or translational control sequences, which will generally be appropriate for the host cell used for expression of the antigen-encoding polynucleotide. Typically, the transcriptional and translational regulatory control sequences include, but are not limited to, a promoter sequence, a 5' non-coding region, a cis-regulatory region such as a functional binding site for transcriptional regulatory protein or translational regulatory protein, an upstream open reading frame, transcriptional start site, translational start site, and/or nucleotide sequence which encodes a leader sequence, termination codon, translational stop site and a 3' non-translated region. Constitutive or inducible promoters as known in the art are contemplated by the invention. The promoters may be either naturally occurring promoters, or hybrid promoters that combine elements of more than one promoter. Promoter sequences contemplated by the present invention may be native to the host cell to be introduced or may be derived from an alternative source, where the region is functional in the host cell.

The expression vector may also comprise a 3' non-translated sequence, which usually refers to that portion of a gene comprising a DNA segment that contains a polyadenylation signal and any other regulatory signals capable of effecting mRNA processing or gene expression. The polyadenylation signal is characterised by effecting the addition of polyadenylic acid tracts to the 3' end of the mRNA precursor. Polyadenylation signals are commonly recognised by the presence of homology to the canonical form 5' AATAAA-3' although variations are not uncommon. The 3' non-translated regulatory DNA sequence typically includes from about 50 to 1,000 nucleotide base pairs and may contain transcriptional and translational termination sequences in addition to a polyadenylation signal and any other regulatory signals capable of effecting mRNA processing or gene expression.

In certain embodiments, the expression vector further contains a selectable marker gene to allow the selection of transformed host cells. Selection genes are well known in the art and will vary with the host cell used.

The expression vector may also include a fusion partner (typically provided by the expression vector) so that the recombinant polypeptide is expressed as a fusion polypeptide with the fusion partner. The main advantage of fusion partners is that they assist identification and/or purification of said fusion polypeptide. Well known examples of fusion partners include, but are not limited to, glutathione-S-transferase (GSI), Fc portion of human IgG, maltose binding protein (MBP) and hexahistidine (HIS$_6$), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with (HIS$_6$) fusion partners and the Pharmacia GST purification system. Preferably, the fusion partners also have protease cleavage sites, such as for Factor X$_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation. Fusion partners also include within their scope "epitope tags", which are usually short peptide sequences for which a specific antibody is available. Well known examples of epitope tags for which specific monoclonal antibodies are readily available include c-Myc, influenza virus haemagglutinin and FLAG tags.

The step of introducing the expression vector into the host cell may be achieved by any suitable method including transfection, transduction of viral vectors, including adenoviral, modified lentiviral and other retroviral vectors, and transformation, the choice of which will be dependent on the host cell employed. Such methods are well known to those of skill in the art.

Recombinant polypeptides may be produced by culturing a host cell transformed with the expression vector under conditions appropriate for protein expression, which will vary with the choice of expression vector and the host cell. This is easily ascertained by one skilled in the art through routine experimentation. Suitable host cells for expression may be prokaryotic or eukaryotic. One preferred host cell for expression of a polypeptide according to the invention is a bacterium. The bacterium used may be *Escherichia coli*. Alternatively, the host cell may be an insect cell such as, for example, SF9 cells that may be utilised with a baculovirus expression system.

In some embodiments, the antigen, which is administered with the lectin-interactive agent of the invention, is in the form of a construct or vector from which it is expressible.

Alternatively, the antigen can be synthesised using solution synthesis or solid phase synthesis as described, for example, by Atherton and Sheppard (Solid Phase Peptide Synthesis: A Practical Approach, IRL Press at Oxford University Press, Oxford, England, 1989) or by Roberge et al. (1995, *Science* 269: 202). The amino acids of the synthesised antigens can be non-naturally occurring or naturally occurring amino acid. Examples of unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. A list of unnatural amino acids contemplated by the present invention is shown in TABLE B.

TABLE B

| Non-conventional amino acid | NON-CONVENTIONAL AMINO ACID |
| --- | --- |
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| cyclohexylalanine | L-N-methylglutamine |
| cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |
| D-glutamate | L-N-methylnorvaline |
| D-glutamic acid | L-N-methylornithine |
| D-histidine | L-N-methylphenylalanine |
| D-isoleucine | L-N-methylproline |
| D-leucine | L-N-medlylserine |

TABLE B-continued

| Non-conventional amino acid | NON-CONVENTIONAL AMINO ACID |
| --- | --- |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcyclopentylalanine |
| D-α-methylasparagine | α-methyl-α-napthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamylediyl)glycine |
| D-α-methylornithiine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |
| D-α-methylthreonine | N-cycloheptyglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvatine | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |
| N-(N-(2,2-diphenylethyl carbamylmethyl)glycine | N-(N-(3,3-diphenylpropyl carbamylmethyl(glycine |
| 1-carboxy-1-(2,2-diphenyl-ethyl amino)cyclopropane | |

The invention also contemplates modifying peptide antigens using ordinary molecular biological techniques so as to alter their resistance to proteolytic degradation or to optimise solubility properties or to render them more suitable as an immunogenic agent.

Peptide antigens may be of any suitable size that can be utilised to stimulate or inhibit an immune response to a target antigen of interest. A number of factors can influence the choice of peptide size. For example, the size of a peptide can be chosen such that it includes, or corresponds to the size of, T cell epitopes and/or B cell epitopes, and their processing requirements. Practitioners in the art will recognise that class I-restricted T cell epitopes are typically between 8 and 10 amino acid residues in length and if placed next to unnatural flanking residues, such epitopes can generally require 2 to 3 natural flanking amino acid residues to ensure that they are efficiently processed and presented. Class II-restricted T cell epitopes usually range between 12 and 25 amino acid residues in length and may not require natural flanking residues for efficient proteolytic processing although it is believed that natural flanking residues may play a role. Another important feature of class II-restricted epitopes is that they generally contain a core of 9-10 amino acid residues in the middle which bind specifically to class II MHC molecules with flanking sequences either side of this core stabilising binding by associating with conserved structures on either side of class II MHC antigens in a sequence independent manner. Thus the functional region of class II-restricted epitopes is typically less than about 15 amino acid residues long. The size of linear B cell epitopes and the factors effecting their processing, like class II-restricted epitopes, are quite variable although such epitopes are frequently smaller in size than 15 amino acid residues. From the foregoing, it is advantageous, but not essential, that the size of the peptide is at least 6, 7, 8, 9, 10, 11, 12, 13, 14, 15, 20, 25, 30 amino acid residues. Suitably, the size of the peptide is no more than about 500, 200, 100, 80, 60, 50, 40 amino acid residues. In certain advantageous embodiments, the size of the peptide is sufficient for presentation by an antigen-presenting cell of a T cell and/or a B cell epitope contained within the peptide.

Criteria for identifying and selecting effective antigenic peptides (e.g., minimal peptide sequences capable of eliciting an immune response) can be found in the art. For example, Apostolopoulos et al. (2000, *Curr. Opin. Mol. Ther.* 2:29-36) discusses the strategy for identifying minimal antigenic peptide sequences based on an understanding of the three dimensional structure of an antigen-presenting molecule and its interaction with both an antigenic peptide and T-cell receptor. Shastri (1996, *Curr. Opin. Immunol.* 8:271-277) discloses how to distinguish rare peptides that serve to activate T cells from the thousands peptides normally bound to MHC molecules.

2.2.2 Immune-Modulating Cell Embodiments

Antigen-Presenting Cells

The present invention also contemplates the use of antigen-presenting cells, which present an antigen corresponding to at least a portion of the target antigen, in the compositions of the present invention. Such antigen-presenting cells include professional or facultative antigen-presenting cells. Professional antigen-presenting cells function physiologically to present antigen in a form that is recognised by specific T cell receptors so as to stimulate or anergise a T lymphocyte or B lymphocyte mediated immune response. Professional antigen-presenting cells not only process and present antigens in the context of the major histocompatability complex (MHC), but also possess the additional immunoregulatory molecules required to complete T cell activation or induce a tolerogenic response. Professional antigen-presenting cells include, but are not limited to, macrophages, monocytes, B lymphocytes, cells of myeloid lineage, including monocytic-granulocytic-DC precursors, marginal zone Kupffer cells, microglia, T cells, Langerhans cells and dendritic cells including interdigitating dendritic cells and follicular dendritic cells. Non-professional or facultative antigen-presenting cells typically lack one or more of the immunoregulatory molecules required to complete T lymphocyte activation or anergy. Examples of non-professional or facultative antigen-presenting cells include, but are not limited to, activated T lymphocytes, eosinophils, keratinocytes, astrocytes, follicular cells, microglial cells, thymic cortical cells, endothelial cells, Schwann cells, retinal pigment epithelial cells, myoblasts, vascular smooth muscle cells, chondrocytes, enterocytes, thymocytes, kidney tubule cells and fibroblasts. In some embodiments, the antigen-presenting cell is selected from monocytes, macrophages, B lymphocytes, cells of myeloid lineage, dendritic cells or Langerhans cells. In certain advantageous embodiments, the antigen-presenting cell expresses CD11c and includes a dendritic cell.

In some embodiments the antigen-presenting cell stimulates an immune response. In other embodiments, the antigen-presenting cell induces a tolerogenic response.

Antigen-presenting cells for stimulating an immune response to an antigen or group of antigens, or for inducing a tolerogenic response including the induction of an anergic response or the suppression of a future or existing immune response, to an antigen or group of antigens may be prepared according to any suitable method known to the skilled practitioner. Illustrative methods for preparing antigen-presenting cells for stimulating antigen-specific immune responses are described by Albert et al. (International Publication WO 99/42564), Takamizawa et al. (1997, *J Immunol*, 158(5): 2134-2142), Thomas and Lipsky (1994, *J Immunol*, 153(9): 4016-4028), O'Doherty et al. (1994, *Immunology*, 82(3):487-93), Fearnley et al. (1997, *Blood*, 89(10): 3708-3716), Weissman et al. (1995, *Proc Natl Acad Sci USA*, 92(3):826-830), Freudenthal and Steinman (1990, *Proc Natl Acad Sci USA*, 87(19):7698-7702), Romani et al. (1996, *Immunol Methods*, 196(2): 137-151), Reddy et al. (1997, *Blood*, 90(9):3640-3646), Thurnher et al. (1997, *Exp Hematol*, 25(3):232-237), Caux et al. (1996, *J Exp Med*, 184(2):695-706; 1996, *Blood*, 87(6):2376-85), Luft et al. (1998, *Exp Hematol*, 26(6):489-500; 1998, *J Immunol*, 161(4):1947-1953), Cella et al. (1999, *J Exp Med*, 189(5): 821-829;1997, *Nature*, 388(644):782-787; 1996, *J Exp Med*, 184(2):747-572), Ahonen et al. (1999, *Cell Immunol*, 197(1):62-72) and Piemonti et al. (1999, *J Immunol*, 162(11):6473-6481). Illustrative methods for preparing antigen-presenting cells for inhibiting immune responses or for inducing tolerogenic responses are described by Ichim et al. (2003, *Transplant Immunol* 11:295-306) including methods for generating killer dendritic cells (DC) by transfections with FasL, generating immature DC by inhibition of NF-κB as described, for example, in International Publication No. WO2004/014056, generation of MHC-inhibited DC by treatment with CLIP and generation of IL-12 gene-silenced CD by post-transcriptional gene silencing or RNA interference.

In some embodiments, the antigen-presenting cells are isolated from a host, treated and then re-introduced or reinfused into the host. Conveniently, antigen-presenting cells can be obtained from the host to be treated either by surgical resection, biopsy, blood sampling, or other suitable technique. Such cells are referred to herein as "autologous" cells. In other embodiments, the antigen-presenting cells or cell lines are prepared and/or cultured from a different source than the host. Such cells are referred to herein as "allogeneic" cells. Desirably, allogeneic antigen-presenting cells or cell lines will share major and/or minor histocompatibility antigens to potential recipients (also referred to herein as 'generic' antigen-presenting cells or cell lines). In certain advantageous embodiments of this type, the generic antigen-presenting cells or cell lines comprise major histocompatibility (MHC) class I antigens compatible with a high percentage of the population (i.e., at least 10, 20, 30, 40, 50, 60, 70, 75, 80, 85, 90, 92, 94 or 98%) that is susceptible or predisposed to a particular condition. Suitably, the generic antigen-presenting cells or cell lines naturally express an immunostimulatory molecule as described herein, especially an immunostimulatory membrane molecule, at levels sufficient to trigger an immune response, desirably a T lymphocyte immune response (e.g., a cytotoxic T lymphocyte immune response), in the intended host. In certain embodiments, the antigen-presenting cells or cell lines are highly susceptible to treatment with at least one IFN as described herein and in International Publication No. WO 01/88097 (i.e., implied high level expression of class I HLA).

In some embodiments, antigen-presenting cells are made antigen-specific by a process including contacting or 'pulsing' the antigen-presenting cells with an antigen that corresponds to at least a portion of the target antigen for a time and under conditions sufficient to permit the antigen to be internalised by the antigen-presenting cells; and culturing the antigen-presenting cells so contacted for a time and under conditions sufficient for the antigen to be processed for presentation by the antigen-presenting cells. The pulsed cells can then be used to stimulate autologous or allogeneic T cells in vitro or in vivo. The amount of antigen to be placed in contact with antigen-presenting cells can be determined empirically by persons of skill in the art. Typically antigen-presenting cells are incubated with antigen for about 1 to 6 hr at 37° C. Usually, for purified antigens and peptides, 0.1-10 µg/mL is suitable for producing antigen-specific antigen-presenting cells. The antigen should be exposed to the antigen-presenting cells for a period of time sufficient for those cells to internalise the antigen. The time and dose of antigen necessary for the cells to internalise and present the processed antigen may be determined using pulse-chase protocols in which exposure to antigen is followed by a washout period and exposure to a read-out system e.g., antigen reactive T cells. Once the optimal time and dose necessary for cells to express processed antigen on their surface is determined, a protocol may be used to prepare cells and antigen for inducing tolerogenic responses. Those of skill in the art will recognise in this regard that the length of time necessary for an antigen-presenting cell to present an antigen may vary depending on the antigen or form of antigen employed, its dose, and the antigen-presenting cell employed, as well as the conditions under which antigen loading is undertaken. These parameters can be determined by the skilled artisan using routine procedures.

The delivery of exogenous antigen to an antigen-presenting cell can be enhanced by methods known to practitioners in the art. For example, several different strategies have been developed for delivery of exogenous antigen to the endogenous processing pathway of antigen-presenting cells, especially dendritic cells. These methods include insertion of antigen into pH-sensitive liposomes (Zhou and Huang, 1994, *Immunomethods*, 4:229-235), osmotic lysis of pinosomes after pinocytic uptake of soluble antigen (Moore et al., 1988, *Cell*, 54:777-785), coupling of antigens to potent adjuvants (Aichele et al., 1990, *J. Exp. Med.*, 171: 1815-1820; Gao et al., 1991, *J. Immunol.*, 147: 3268-3273; Schulz et al., 1991, *Proc. Natl. Acad. Sci. USA*, 88: 991-993; Kuzu et al., 1993, *Euro. J. Immunol.*, 23: 1397-1400; and Jondal et al., 1996, *Immunity* 5: 295-302) and apoptotic cell delivery of antigen (Albert et al. 1998, *Nature* 392:86-89; Albert et al. 1998, *Nature Med.* 4:1321-1324; and in International Publications WO 99/42564 and WO 01/85207). Recombinant bacteria (eg. *E. coli*) or transfected host mammalian cells may be pulsed onto dendritic cells (as particulate antigen, or apoptotic bodies respectively) for antigen delivery. Recombinant chimeric virus-like particles (VLPs) have also been used as vehicles for delivery of exogenous heterologous antigen to the MHC class I processing pathway of a dendritic cell line (Bachmann et al., 1996, *Eur. J. Immunol.*, 26(11): 2595-2600).

Alternatively, or in addition, an antigen may be linked to, or otherwise associated with, a cytolysin to enhance the transfer of the antigen into the cytosol of an antigen-presenting cell of the invention for delivery to the MHC class I pathway. Exemplary cytolysins include saponin compounds such as saponin-containing Immune Stimulating Complexes (ISCOMs) (see e.g., Cox and Coulter, 1997, *Vaccine* 15(3): 248-256 and U.S. Pat. No. 6,352,697), phospholipases (see, e.g., Camilli et al., 1991, *J. Exp. Med.* 173: 751-754), pore-forming toxins (e.g., an α-toxin), natural cytolysins of gram-positive bacteria, such as listeriolysin O (LLO, e.g., Mengaud et al., 1988, *Infect. Immun.* 56: 766-772 and Portnoy et al., 1992, *Infect. Immun.* 60: 2710-2717), streptolysin O (SLO, e.g., Palmer et al., 1998, *Biochemistry* 37(8): 2378-2383) and perfringolysin (PFO, e.g., Rossjohn et al., *Cell* 89(5): 685-692). Where the antigen-presenting cell is phagosomal, acid activated cytolysins may be advantageously used. For example, listeriolysin exhibits greater pore-forming ability at mildly acidic pH (the pH conditions within the phagosome), thereby facilitating delivery of vacuole (including phagosome and endosome) contents to the cytoplasm (see, e.g., Portnoy et al., *Infect. Immun.* 1992, 60: 2710-2717).

The cytolysin may be provided together with a pre-selected antigen in the form of a single composition or may be provided as a separate composition, for contacting the antigen-presenting cells. In one embodiment, the cytolysin is fused or otherwise linked to the antigen, wherein the fusion or linkage permits the delivery of the antigen to the cytosol of the target cell. In another embodiment, the cytolysin and antigen are provided in the form of a delivery vehicle such as, but not limited to, a liposome or a microbial delivery vehicle selected from virus, bacterium, or yeast. Suitably, when the delivery vehicle is a microbial delivery vehicle, the delivery vehicle is non-virulent. In a preferred embodiment of this type, the delivery vehicle is a non-virulent bacterium, as for example described by Portnoy et al. in U.S. Pat. No. 6,287,556, comprising a first polynucleotide encoding a non-secreted functional cytolysin operably linked to a regulatory polynucleotide which expresses the cytolysin in the bacterium, and a second polynucleotide encoding one or more pre-selected antigens. Non-secreted cytolysins may be provided by various mechanisms, e.g., absence of a functional signal sequence, a secretion incompetent microbe, such as microbes having genetic lesions (e.g., a functional signal sequence mutation), or poisoned microbes, etc. A wide variety of non-virulent, non-pathogenic bacteria may be used; preferred microbes are relatively well characterised strains, particularly laboratory strains of *E. coli*, such as MC4100, MC1061, DH5α, etc. Other bacteria that can be engineered for the invention include well-characterised, nonvirulent, non-pathogenic strains of *Listeria monocytogelies, Shigella flexneri*, mycobacterium, *Salmonella, Bacillus subtilis*, etc. In a particular embodiment, the bacteria are attenuated to be non-replicative, non-integrative into the host cell genome, and/or non-motile inter- or intra-cellularly.

The delivery vehicles described above can be used to deliver one or more antigens to virtually any antigen-presenting cell capable of endocytosis of the subject vehicle, including phagocytic and non-phagocytic antigen-presenting cells. In embodiments when the delivery vehicle is a microbe, the subject methods generally require microbial uptake by the target cell and subsequent lysis within the antigen-presenting cell vacuole (including phagosomes and endosomes).

In other embodiments, the antigen is produced inside the antigen-presenting cell by introduction of a suitable expression vector as for example described above. The antigen-encoding portion of the expression vector may comprise a naturally-occurring sequence or a variant thereof, which has been engineered using recombinant techniques. In one example of a variant, the codon composition of an antigen-encoding polynucleotide is modified to permit enhanced expression of the antigen in a target cell or tissue of choice using methods as set forth in detail in International Publications WO 99/02694 and WO 00/42215. Briefly, these methods are based on the observation that translational efficiencies of different codons vary between different cells or tissues and that these differences can be exploited, together with codon composition of a gene, to regulate expression of a protein in a particular cell or tissue type. Thus, for the construction of codon-optimised polynucleotides, at least one existing codon of a parent polynucleotide is replaced with a synonymous codon that has a higher translational efficiency in a target cell or tissue than the existing codon it replaces. Although it is preferable to replace all the existing codons of a parent nucleic acid molecule with synonymous codons which have that higher translational efficiency, this is not necessary because increased expression can be accomplished even with partial replacement. Suitably, the replacement step affects 5, 10, 15, 20, 25, 30%, more preferably 35, 40, 50, 60, 70% or more of the existing codons of a parent polynucleotide.

The expression vector for introduction into the antigen-presenting cell will be compatible therewith such that the antigen-encoding polynucleotide is expressible by the cell. For example, expression vectors of this type can be derived from viral DNA sequences including, but not limited to, adenovirus, adeno-associated viruses, herpes-simplex viruses and retroviruses such as B, C, and D retroviruses as well as spumaviruses and modified lentiviruses. Suitable expression vectors for transfection of animal cells are described, for example, by Wu and Ataai (2000, *Curr. Opin. Biotechnol.* 11(2):205-208), Vigna and Naldini (2000, *J. Gene Med.* 2(5): 308-316), Kay, et al. (2001, *Nat. Med.* 7(1):33-40), Athanasopoulos, et al. (2000, *Int. J. Mol. Med.* 6(4):363-375) and Walther and Stein (2000, *Drugs* 60(2):249-271). The expression vector is introduced into the antigen-presenting cell by any suitable means which will be dependent on the particular choice of expression vector and antigen-presenting cell employed. Such means of introduction are well-known to those skilled in the art. For example, introduction can be effected by use of contacting (e.g., in the case of viral vectors), electroporation, transformation, transduction, conjugation or triparental mating, transfection, infection membrane fusion with cationic lipids, high-velocity bombardment with DNA-coated microprojectiles, incubation with calcium phosphate-DNA precipitate, direct microinjection into single cells, and the like. Other methods also are available and are known to those skilled in the art. Alternatively, the vectors are introduced by means of cationic lipids, e.g., liposomes. Such liposomes are commercially available (e.g., Lipofectin®, Lipofectamine™, and the like, supplied by Life Technologies, Gibco BRL, Gaithersburg, Md.). It will be understood by persons of skill in the art that the techniques for assembling and expressing antigen-encoding nucleic acid molecules, immunoregulatory molecules and/or cytokines as described herein e.g., synthesis of oligonucleotides, nucleic acid amplification techniques, transforming cells, constructing vectors, expressions system and the like and transducing or otherwise introducing nucleic acid molecules into cells are well established in the art, and most practitioners are familiar with the standard resource materials for specific conditions and procedures.

In some embodiments, the antigen-specific antigen-presenting cells are obtained by isolating antigen-presenting cells or their precursors from a cell population or tissue to which modification of an immune response is desired. Typically, some of the isolated antigen-presenting cells or precursors will constitutively present antigens or have taken up such antigen in vivo that are targets or potential targets of an immune response for which stimulation or inhibition of an immune response is desired. In this instance, the delivery of exogenous antigen is not essential. Alternatively, cells may be derived from biopsies of healthy or diseased tissues, lysed or rendered apoptotic and the pulsed onto antigen-presenting cells (e.g., dendritic cells). In certain embodiments of this type, the antigen-presenting cells are cancer or tumour cells to which an antigen-specific immune response is required. Illustrative examples of cancers or tumour cells include cells of sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumour, cervical cancer, testicular tumour, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; myelomonocytic, monocytic and erythroleukemia); chronic leukemia (chronic myelocytic (granulocyte) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In certain embodiments, the cancer or tumour cells are selected from the group melanoma cells and mammary carcinoma cells.

In some of the above embodiments, the cancer or tumour cells will constitute facultative or non-professional antigen-presenting cells, and may in some instances require firther modification to enhance their antigen-presenting functions. In these instances, the antigen-presenting cells are further modified to express one or more immunoregulatory molecules, which include any molecules occurring naturally in animals that may regulate or directly influence immune responses including: proteins involved in antigen processing and presentation such as TAP1/TAP2 transporter proteins, proteosome molecules such as LMP2 and LMP7, heat shock proteins such as gp96, HSP70 and HSP90, and major histocompatibility complex (MHC) or human leucocyte antigen (HLA) molecules; factors that provide co-stimulation signals for T cell activation such as B7 and CD40; factors that provide co-inhibitory signals for direct killing of T cells or induction of T lymphocyte or B lymphocyte anergy or stimulation of T regulatory cell (Treg) generation such as OX-2, programmed death-1 ligand (PD-1L); accessory molecules such as CD83; chemokines; lymphokines and cytokines such as interferons $\alpha$, $\beta$ and $\gamma$, interleukins (e.g., IL-2, IL-7, IL-12, IL-15, IL-22, etc.), factors stimulating cell growth (e.g., GM-SCF) and other factors (e.g., tumour necrosis factors (INFs), DC-SIGN, MIP1$\alpha$, MIP1$\beta$ and transforming growth factor-$\beta$ (TGF-$\beta$). In certain advantageous embodiments, the immunoregulatory molecules are selected from a B7 molecule (e.g., B7-1, B7-2 or B7-3) and an ICAM molecule (e.g., ICAM-1 and ICAM-2).

Instead of recombinantly expressing immunoregulatory molecules, antigen-presenting cells expressing the desired immunostimulatory molecule(s) may be isolated or selected from a heterogeneous population of cells. Any method of isolation/selection is contemplated by the present invention, examples of which are known to those of skill in the art. For instance, one can take advantage of one or more particular characteristics of a cell to specifically isolate that cell from a heterogeneous population. Such characteristics include, but are not limited to, anatomical location of a cell, cell density, cell size, cell morphology, cellular metabolic activity, cell uptake of ions such as $Ca^{2+}$, $K^+$, and $H^+$ ions, cell uptake of compounds such as stains, markers expressed on the cell surface, protein fluorescence, and membrane potential. Suitable methods that can be used in this regard include surgical removal of tissue, flow cytometry techniques such as fluorescence-activated cell sorting (FACS), immunoaffinity separation (e.g., magnetic bead separation such as Dynabead™ separation), density separation (e.g., metrizamide, Percoll™, or Ficoll™ gradient centrifugation), and cell-type specific density separation. Desirably, the cells are isolated by flow cytometry or by immunoaffinity separation using an antigen-binding molecule that is immuno-interactive with the immunoregulatory molecule.

Alternatively, the immunoregulatory molecule can be provided to the antigen-presenting cells in soluble form. In some embodiments of this type, the immunoregulatory molecule is a B7 molecule that lacks a functional transmembrane domain (e.g., that comprises a B7 extracellular domain), non-limiting examples of which are described by McHugh et al. (1998, *Clin. Immunol. Immunopathol* 87(1):50-59), Faas et al. (2000, *J. Immunol.* 164(12):6340-6348) and Jeannin et al. (2000, *Immunity* 13(3):303-312). In other embodiments of this type, the immunostimulatory protein is a B7 derivative including, but not limited to, a chimeric or fusion protein comprising a B7 molecule, or biologically active fragment thereof, or variant or derivative of these, linked together with an antigen binding molecule such as an immunoglobulin molecule or biologically active fragment thereof. For example, a polynucleotide encoding the amino acid sequence corresponding to the extracellular domain of the B7-1 molecule, containing amino acids from about position 1 to about position 215, is joined to a polynucleotide encoding the amino acid sequences corresponding to the hinge, CH2 and CH3 regions of human Ig Cγ1, using PCR, to form a construct that is expressed as a B7Ig fusion protein. DNA encoding the amino acid sequence corresponding to a B7Ig fusion protein has been deposited with the American Type culture Collection (ATCC) in Rockville, Md., under the Budapest Treaty on May 31, 1991 and accorded accession number 68627. Techniques for making and assembling such B7 derivatives are disclosed for example by Linsley et al. (U.S. Pat. No. 5,580, 756). Reference also may be made to Sturmhoefel et al. (1999, *Cancer Res.* 59: 4964-4972) who disclose fusion proteins comprising the extracellular region of B7-1 or B7-2 fused in frame to the Fc portion of IgG2a.

The half-life of a soluble immunoregulatory molecule may be prolonged by any suitable procedure if desired. Preferably, such molecules are chemically modified with polyethylene glycol (PEG), including monomethoxy-polyethylene glycol, as for example disclosed by Chapman et al (1999, *Nature Biotechnology* 17: 780-783).

Alternatively, or in addition, the antigen-presenting cells are cultured in the presence of at least one interferon for a time and under conditions sufficient to enhance the antigen presenting function of the cells and washing the cells to remove the interferon(s). In certain advantageous embodiments of this type, the step of culturing may comprise contacting the cells with at least one type I interferon and/or a type II interferon. The at least one type I interferon is suitably selected from the group consisting of an IFN-α, an IFN-β, a biologically active fragment of an IFN-α, a biologically active fragment of an IFN-β, a variant of an IFN-α, a variant of an IFN-β, a variant of a said biologically active fragment, a derivative of an IFN-α, a derivative of an IFN-β, a derivative of a said biologically active fragment, a derivative of a said variant, an analogue of IFN-α and an analogue of IFN-β. Typically, the type II interferon is selected from the group consisting of an IFN-γ; a biologically active fragment of an IFN-γ, a variant of an IFN-γ, a variant of said biologically active fragment, a derivative of an IFN-γ, a derivative of said biologically active fragment, a derivative of said variant and an analogue of an IFN-γ. Exemplary methods and conditions for enhancing the antigen-presenting functions of antigen-presenting cells using interferon treatment are described in International Publication No. WO 01/88097.

In some embodiments, the antigen-presenting cells (e.g., cancer cells) or cell lines are suitably rendered inactive to prevent further proliferation once administered to the subject. Any physical, chemical, or biological means of inactivation may be used, including but not limited to irradiation (generally with at least about 5,000 cGy, usually at least about 10,000 cGy, typically at least about 20,000 cGy); or treatment with mitomycin-C (usually at least 10 µg/mL; more usually at least about 50 µg/mL).

The antigen-presenting cells may be obtained or prepared to contain and/or express one or more antigens by any number of means, such that the antigen(s) or processed form(s) thereof, is (are) presented by those cells for potential modulation of other immune cells, including T lymphocytes and B lymphocytes, and particularly for producing T lymphocytes and B lymphocytes that are primed to respond to a specified antigen or group of antigens.

Immune-Effector Cells

In some embodiments, the antigen-presenting cells described above are useful for producing primed T lymphocytes to an antigen or group of antigens. In other embodiments, the antigen-specific antigen-presenting cells are useful for producing T lymphocytes that exhibit tolerance/anergy to an antigen or group of antigens. The efficiency of inducing lymphocytes, especially T lymphocytes, to exhibit an immune response or tolerance/anergy to a specified antigen can be determined by any suitable method including, but not limited to, assaying T lymphocyte cytolytic activity in vitro using for example antigen-specific antigen-presenting cells as targets of antigen-specific cytolytic T lymphocytes (CTL); assaying antigen-specific T lymphocyte proliferation (see, e.g., Vollenweider and Groseurth, 1992, *J. Immunol. Meth.* 149: 133-135), measuring B cell response to the antigen using, for example, ELISPOT assays, and ELISA assays; interrogating cytokine profiles; or measuring delayed-type hypersensitivity (DTH) responses by test of skin reactivity to a specified antigen (see, e.g., Chang et al. (1993, *Cancer Res.* 53: 1043-1050). Other methods known to practitioners in the art, which can detect the presence of antigen on the surface of antigen-presenting cells after exposure to the antigen, are also contemplated by the present invention.

Accordingly, the present invention also provides antigen-specific B or T lymphocytes, especially T lymphocytes, which respond in an antigen-specific fashion to representation of the antigen. In some embodiments, antigen-specific T lymphocytes are produced by contacting an antigen-presenting cell as defined above with a population of T lymphocytes, which may be obtained from any suitable source such as spleen or tonsil/lymph nodes but is preferably obtained from peripheral blood. The T lymphocytes can be used as crude preparations or as partially purified or substantially purified preparations, which are suitably obtained using standard techniques as, for example, described in "Immunochemical Techniques, Part G: Separation and Characterization of Lymphoid Cells" (*Meth. in Enzymol.* 108, Edited by Di Sabato et al., 1984, Academic Press). This includes rosetting with sheep red blood cells, passage across columns of nylon wool or plastic adherence to deplete adherent cells, immunomagnetic or flow cytometric selection using appropriate monoclonal antibodies is known in the art.

The preparation of T lymphocytes is contacted with antigen-specific antigen-presenting cells as described herein for an adequate period of time for priming or anergising the T lymphocytes to the antigen or antigens presented by those antigen-presenting cells. This period will usually be at least about 1 day, and up to about 5 days.

In embodiments employing tolerance or anergy inducing antigen-specific antigen-presenting cells, the antigen-specific anergy induced by such cells desirably involves the induction of one or more types of antigen-specific regulatory lymphocytes, especially regulatory T lymphocytes. Several populations of regulatory T lymphocytes are known to inhibit the response of other (effector) lymphocytes in an antigen-specific manner including, for example, Tr1 lymphocytes, Th3 lymphocytes, Th2 lymphocytes, CD8$^+$CD28$^-$ regulatory T lymphocytes, CD4$^+$CD25$^+$ regulatory T lymphocytes, natural killer (NK) T lymphocytes and γδ T lymphocytes.

Tr1 lymphocytes can emerge after several rounds of stimulation of human blood T cells by allogeneic monocytes in the presence of IL-10. This subpopulation secretes high levels of IL-10 and moderate levels of TGFβ but little IL-4 or IFNγ (Groux et al., 1997, *Nature* 389:737-742).

The Th3 regulatory subpopulation refers to a specific subset induced following antigen delivery via the oral (or other mucosal) route. They produce predominantly TGFβ, and only low levels of IL-10, IL-4 or IFNγ, and provide specific help for IgA production (Weiner et al., 2001, *Microbes Infect* 3:947-954). They are able to suppress both Th1 and Th2-type effector T cells.

Th2 lymphocytes produce high levels of IL-4, IL-5 and IL-10 but low IFNγ and TGFβ. Th2 lymphocytes are generated in response to a relative abundance of IL-4 and lack of IL-12 in the environment at the time of presentation of their cognate peptide ligands (O'Garra and Arai, 2000, *Trends Cell Biol* 10:542-550). T lymphocyte signalling by CD86 may also be important for generation of Th2 cells (Lenschow et al., 1996, *Immunity* 5:285-293; Xu et al., 1997, *J Immunol* 159:4217-4226).

A distinct CD8$^+$CD28$^-$ regulatory or "suppressor" subset of T lymphocytes can be induced by repetitive antigenic stimulation in vitro. They are MHC class I-restricted, and suppress CD4$^+$ T cell responses.

CD4$^+$ CD25$^+$ regulatory or "suppressor" subset of T lymphocytes inhibit a variety of autoimmnune and inflammatory diseases and they are also efficient in the suppression of alloantigen responses. In particular, these lymphocytes can down-regulate the immune response by affecting T cell responses, antibody production, cytokine secretion and antigen-presenting cells (see for example Suvas et al., 2003, *J Exp Med.* 198(6):889-901; Taams et al., 2003, *Transpl Immunol.* 11(34):277-85; Jonuleit et al., 2003, *Transpl Immunol.* 11(3-4):267-76; Green et al. 2003, *Proc Natl Acad Sci USA.* 100 (19):10878-10883). CD4+CD25+ regulatory T cells are generated by repetitive antigenic stimulation in vitro (Feunou et al., 2003, *J Immunol.* 171(7):3475-84).

NK T lymphocytes, which express the NK cell marker, CD161, and whose TCR are Vα24JαQ in human and Vα14Jα281 in mouse, are activated specifically by the non-polymorphic CD1d molecule through presentation of a glycolipid antigen (Kawano et al., 1997, *Science* 278:1626-1629). They have been shown to be immunoregulatory in a number of experimental systems. They are reduced in number in several autoimmune models before disease onset, and can reduce incidence of disease upon passive transfer to non-obese diabetic (NOD) mice. Administration of the glycolipid, α-galactosyl ceramide (α-gal cer), presented by CD1d, also results in accumulation of NKT lymphocytes and amelioration of diabetes in these mice (Naumov et al., 2001, *Proc Natl Acad Sci USA* 98:13838-13843).

γδ T lymphocytes have been implicated in the downregulation of immune responses in various inflammatory diseases and in the suppression of inflammation associated with induction of mucosal tolerance. The tolerance induced by mucosal antigen was transferable to untreated recipient mice by small numbers of γδ T cells (McMenamin et al., 1995, *J Immunol* 154:4390-4394; McMenamin et al., 1994, *Science* 265:1869-1871). Moreover, mucosal tolerance induction was blocked by the administration of the GL3 antibody that blocks yS T cell function (Ke et al., 1997, *J Immunol* 158:3610-3618).

Whether the antigen-specific T lymphocytes are produced in contact with antigen-presenting cells in vitro or in vivo, the antigen-specific anergy induced by the antigen-presenting cells reflects the inability of the antigen-specific lymphocytes to respond to subsequent restimulation with the specific antigen. These antigen-specific lymphocytes are suitably characterised by production of IL-10 in an antigen-specific manner. IL-10 is a cytokine with potent immunosuppressive properties. IL-10 inhibits antigen-specific T lymphocyte proliferation at different levels. IL-10 inhibits the antigen-presenting and accessory cell function of professional antigen-presenting cells such as monocytes, dendritic cells and Langerhans cells by downregulation of the expression of MHC class II molecules and of the adhesion and co-stimulatory molecules ICAM-1 and B7.1 and B7.2 (reviewed in Interleukin 10, de Vries and de Waal Malefyt, eds., Landes Co, Austin Tex., 1995). IL-10 also inhibits IL-12 production by these cells. IL-12 promotes T lymphocyte activation and the differentiation of Th1 lymphocytes (D'Andrea, et al., 1993, *J. Exp. Med.* 178:1041-1048; Hsieh et al., 1993, *Science* 260:547-549). In addition, IL-10 directly inhibits T lymphocyte proliferation by inhibiting IL-2 gene transcription and IL-2 production by these cells (reviewed in Interleukin 10, de Vries and de Waal Malefyt, eds., Landes Co, Austin Tex., (1995)), and itself promotes antigen-presenting cells that induce regulatory T cells (U.S. Pat. No. 6,277,635). Thus, in some embodiments, the presence of anergic T lymphocytes may be determined by assaying IL-10 production, e.g. by ELISA in cell supernatants, or by flow cytometric analysis of intracellular staining.

2.2.3 Antigen-Binding Molecules

The invention also contemplates the use of antigen-binding molecules that are specifically immuno-interactive with a selected target antigen as immune-modulating agents. In some embodiments, the target antigen is expressed in a disease or condition or by a specific pathogen for which an enhanced immune response is required. In other embodiments, the target antigen is aberrantly expressed, typically at a higher level in the disease or condition as compared to the normal state or to a state in which the disease or condition is absent. The antigen-binding molecule is suitably interactive with a target antigen as described for example in Section 2.2.1. Numerous antigen-binding molecule useful in the present invention are known in the art. In an illustrative example in which colon cancer is the subject of the treatment, the antigen-binding molecule is immuno-interactive with an antigen selected from the Cripto-1protein, Pim-1 protein or an antigen present in a colon cancer cell lysate, as disclosed, for example, in United States Patent Application Publication No. 20040176576.

In some embodiments, the antigen-binding molecule is a whole polyclonal antibody. Such antibodies may be prepared, for example, by injecting an antigen that corresponds to at least a portion of the target antigen into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, (John Wiley & Sons, Inc, 1991), and Ausubel et al., (1994-1998, supra), in particular Section III of Chapter 11.

In lieu of polyclonal antisera obtained in a production species, monoclonal antibodies may be produced using the standard method as described, for example, by Köhler and Milstein (1975, Nature 256, 495-497), or by more recent modifications thereof as described, for example, in Coligan et al., (1991, supra) by immortalising spleen or other antibody producing cells derived from a production species which has been inoculated with one or more antigens as described above.

The invention also contemplates as antigen-binding molecules Fv, Fab, Fab' and F(ab)$_2$ immunoglobulin fragments. Alternatively, the antigen-binding molecule may comprise a synthetic stabilised Fv fragment. Exemplary fragments of this type include single chain Fv fragments (sFv, frequently termed scFv) in which a peptide linker is used to bridge the N terminus or C terminus of a $V_H$ domain with the C terminus or N-terminus, respectively, of a $V_L$ domain. ScFv lack all constant parts of whole antibodies and are not able to activate complement. ScFvs may be prepared, for example, in accordance with methods outlined in Kreber et al. (Kreber et al. 1997, J. Immunol. Methods; 201(1): 35-55). Alternatively, they may be prepared by methods described in U.S. Pat. No. 5,091,513, European Patent No 239,400 or the articles by Winter and Milstein (1991, Nature 349:293) and Plückthun et al. (1996, In *Antibody engineering: A practical approach*. 203-252). In another embodiment, the synthetic stabilised Fv fragment comprises a disulphide stabilised Fv (dsFv) in which cysteine residues are introduced into the $V_H$ and $V_L$ domains such that in the fully folded Fv molecule the two residues will form a disulphide bond between them. Suitable methods of producing dsFv are described for example in (Glockscuther et al. *Biochem.* 29: 1363-1367; Reiter et al. 1994, *J. Biol. Chem.* 269: 18327-18331; Reiter et al. 1994, *Biochem.* 33: 5451-5459; Reiter et al. 1994. *Cancer Res.* 54: 2714-2718; Webber et al. 1995, *Mol. Immunol.* 32: 249-258).

2.3 Ancillary Components

In some embodiments the composition further comprises one or more cytokines, which are suitably selected from flt3, SCF, IL-3, IL-6, GM-CSF, G-CSF, TNF-α, IL-4, TNF-β, LT-β, IL-2, IL-7, IL-9, IL-15, IL-13, IL-5, IL-1α, IL-1β, IFN-γ, IL-10, IL-17, IL-16, IL-18, HGF, IL-11, MSP, FasL, TRAIL, TRANCE, LIGHT, TWEAK, CD27L, CD30L, CD40L, APRIL, TALL-1, 4-1BBL, OX40L, GITRL, IGF-I, IGF-II, HGF, MSP, FGF-a, FGF-b, FGF-3-19, NGF, BDNF, NTs, Tpo, Epo, Ang1-4, PDGF-AA, PDGF-BB, VEGF-A, VEGF-B, VEGF-C, VEGF-D, PlGF, EGF, TGF-α, AR, BTC, HRGs, HB-EGF, SMDF, OB, CT-1, CNTF, OSM, SCF, Flt-3L, M-CSF, MK and PTN or their functional, recombinant or chemical equivalents or homologues thereof. Preferably the cytokine is selected from the group consisting of IL-12, IL-3, IL-5, TNF, GMCSF, and IFN-γ.

3. Cell Based Therapy Prophylaxis

In accordance with the present invention, the lectin-interactive agent described in Section 2.1 can be administered to a patient, together with antigen-presenting cells and/or immune effector cells as described in Section 2.2.2 for modulating an immune response, e.g., for priming an immune response or inducing a tolerogenic immune response to one or more cognate antigens. These cell based compositions are useful, therefore, for treating or preventing a disease or condition that is associated with the presence or aberrant expression of a target antigen. The cells of the invention can be introduced into a patient by any means (e.g., injection), which produces the desired immune response to an antigen or group of antigens. The cells may be derived from the patient (i.e., autologous cells) or from an individual or individuals who are MHC matched or mismatched (i.e., allogeneic) with the patient. Typically, autologous cells are injected back into the patient from whom the source cells were obtained. The injection site may be subcutaneous, intraperitoneal, intramuscular, intradermal, or intravenous. The cells may be administered to a patient already suffering from a disease or condition or who is predisposed to a disease or condition in sufficient number to treat or prevent or alleviate the symptoms of the disease or condition. The number of cells injected into the patient in need of the treatment or prophylaxis may vary depending on inter alia, the antigen or antigens and size of the individual. This number may range for example between about $10^3$ and $10^{11}$, and usually between about $10^5$ and $10^7$ cells (e.g., dendritic cells or T lymphocytes). Single or multiple administrations of the cells can be carried out with cell numbers and pattern being selected by the treating physician. The cells should be administered in a pharmaceutically acceptable carrier, which is non-toxic to the cells and the individual. Such carrier may be the growth medium in which the cells were grown, or any suitable buffering medium such as phosphate buffered saline. The cells may be administered alone or as an adjunct therapy in conjunction with other therapeutics known in the art for the treatment or prevention of unwanted immune responses for example but not limited to glucocorticoids, methotrexate, D-penicillamine, hydroxychloroquine, gold salts, sulfasalazine, TNFα or interleukin-1 inhibitors, and/or other forms of specific immunotherapy.

4. Pharmaceutical Formulations

The present invention also contemplates immunomodulating formulations, including vaccines, comprising the lectin-binding agent as described in Section 2.1 and an immune-modulating agent e.g., an antigen as described in Sections 2.2.1, an immune effector cell as described in Section 2.2.2 or an antigen-binding molecule as described in Section 2.2.3, or combinations thereof (therapeutic/prophylacetic agents) as active ingredients for the treatment or prophylaxis of various diseases or conditions associated with the presence or aberrant expression of a target antigen. These therapeutic/prophylacetic agents can be administered to a patient either by themselves, or in formulations where they are mixed with a suitable pharmaceutically acceptable carrier and/or diluent, or an adjuvant.

The preparation of such formulations uses routine methods known to persons skilled in the art. Typically, such formulations and vaccines are prepared as injectables, either as liquid solutions or suspensions; solid forms suitable for solution in, or suspension in, liquid prior to injection may also be prepared. The preparation may also be emulsified. The active immunogenic ingredients are often mixed with excipients that are pharmaceutically acceptable and compatible with the active ingredient. Suitable excipients are, for example, water, phosphate buffered saline, saline, dextrose, glycerol, ethanol, or the like and combinations thereof. In addition, if desired, the vaccine may contain minor amounts of auxiliary substances such as wetting or emulsifying agents, pH buffering agents, and/or adjuvants that enhance the effectiveness of the vaccine. Examples of adjuvants which may be effective include but are not limited to: surface active substances such as hexadecylamine, octadecylamine, octadecyl amino acid esters, lysolecithin, dimethyldioctadecylammonium bromide, N,N-dicoctadecyl-N', N'bis(2-hydroxyethylpropanediamine), methoxyhexadecylglycerol, and pluronic polyols; polyamines such as pyran, dextransulfate, poly IC carbopol; mineral gels such as aluminum phosphate, aluminium hydroxide or alum; peptides such as muramyl dipeptide and derivatives such as N-acetyl-muramyl-L-threonyl-D-isoglutamine (thur-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 1.983A, referred to as MTP-PE), and RIBI, which contains three components extracted from bacteria, monophosphoryl lipid A, dimethylglycine, tuftsin; oil emulsions; trehalose dimycolate and cell wall skeleton (MPL+TDM+CWS) in a 2% squalene/Tween 80 emulsion; lymphokines; QuiLA and immune stimulating complexes (ISCOMS). For example, the effectiveness of an adjuvant may be determined by measuring the amount of antibodies resulting from the administration of the vaccine, wherein those antibodies are directed against one or more antigens presented by the treated cells of the vaccine.

The active ingredients should be administered in a pharmaceutically acceptable carrier, which is non-toxic to the cells and the individual to be treated. Such carrier may be the growth medium in which the cells were grown. Compatible excipients include isotonic saline, with or without a physiologically compatible buffer like phosphate or Hepes and nutrients such as dextrose, physiologically compatible ions, or amino acids, and various culture media suitable for use with cell populations, particularly those devoid of other immunogenic components. Carrying reagents, such as albumin and blood plasma fractions and nonactive thickening agents, may also be used. Non-active biological components, to the extent that they are present in the vaccine, are preferably derived from a syngeneic animal or human as that to be treated, and are even more preferably obtained previously from the subject. The injection site may be subcutaneous, intraperitoneal, intramuscular, intradermal, or intravenous.

If soluble actives are employed, the soluble active ingredients can be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic basis such as, for example, sodium, potassium, ammonium, calcium, or ferric hydroxides, and such organic basis as isopropylamine, trimethylamine, 2-ethylamino ethanol, histidine, procaine, and the like.

If desired, devices or pharmaceutical compositions or compositions containing the vaccine and suitable for sustained or intermittent release could be, in effect, implanted in the body or topically applied thereto for the relatively slow release of such materials into the body.

Techniques for formulation and administration may be found in 'Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

The dosage to be administered may depend on the subject to be treated inclusive of the age, sex, weight and general health condition thereof. The dosage will also take into consideration the binding affinity of the lectin-interactive agent to the lectins, its bioavailability and its in vivo and pharmacokinetic properties. In this regard, precise amounts of the agent(s) for administration can also depend on the judgement of the practitioner. In determining the effective amount of the agent(s) to be administered in the treatment of a disease or condition, the physician or veterinarian may evaluate the progression of the disease or condition over time. In any event, those of skill in the art may readily determine suitable dosages of the agents of the invention without undue experimentation. Cell-containing compositions and vaccines are suitably administered to a patient in the range of between about $10^4$ and $10^{10}$, and more preferably between about $10^6$ and $10^8$ treated cells/administration. The dosage of the actives administered to a patient should be sufficient to effect a beneficial response in the patient over time such as a reduction in the symptoms associated with the cancer or tumour. For example usual patient dosages for systemic administration of carbohydrate lectin-interactive agents range from 0.1-200 g/day, typically from 1-160 g/day and more typically from 10-70 g/day. Stated in terms of patient body weight, usual dosages range from 1.5-3000 mg/kg/day, typically from 15-2500 mg/kg/day and more typically from 150-1000 mg/kg/day.

5. Methods for Modulating Immune Responses

The compositions of the invention may be used for modulating an immune response in a subject. Thus, in one embodiment there is provided a method for enhancing an immune response in a subject by administering to the subject the compositions or vaccines of the invention. Advantageously, the immune response is a cell-mediated immune response (e.g., a T-cell mediated response, which desirably includes CD4+ and/or CD8+ T cells).

The active ingredients of the compositions may be administered either sequentially, simultaneously or separately.

Also encapsulated by the present invention is a method for treatment and/or prophylaxis of a disease or condition, comprising administering to a patient in need of such treatment an effective amount of a composition as broadly described above. In certain embodiments, the composition is designed to stimulate or augment an immune response to a target antigen. In these embodiments, the target antigen is typically associated with or responsible for a disease or condition which is suitably selected from cancers, infectious diseases and diseases characterised by immunodeficiency. Examples of cancer include but are not limited to ABL1 protooncogene, AIDS related cancers, acoustic neuroma, acute lymphocytic leukaemia, acute myeloid leukaemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumours, breast cancer, CNS tumours, carcinoid tumours, cervical cancer, childhood brain tumours, childhood cancer, childhood leukaemia, childhood soft tissue sarcoma, chondrosarcoma, choriocarcinoma, chronic lymphocytic leukaemia, chronic myeloid leukaemia, colorectal cancers, cutaneous T-cell lymphoma, dermatofibrosarcoma-protuberans, desmoplastic-small-round-cell-tumour, ductal carcinoma, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anaemia, fibrosarcoma, gall bladder cancer, gastric cancer, gastrointestinal cancers, gastrointestinal-carcinoid-tumour, genitourinary cancers, germ cell tumours, gestational-trophoblastic-disease, glioma, gynaecological cancers, haematological malignancies, hairy cell leukaemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukaemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumour-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer-(NSCLC), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumours, pituitary cancer, polycythemia vera, prostate cancer, rare-cancers-and-associated-disorders, renal cell carcinoma, retinoblastoma, rhabdomyosarcoma, Rothmund-thomson syndrome, salivary gland cancer, sarcoma, schwannoma, Sezary syndrome, skin cancer, small cell lung cancer (SCLC), small intestine cancer, soft tissue sarcoma, spinal cord tumours, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's-macroglobulinemia, Wilms' tumour.

In other embodiments, the composition of the invention could also be used for generating large numbers of $CD8^+$ or CD4+CTL, for adoptive transfer to immunodeficient individuals who are unable to mount normal immune responses. For example, antigen-specific $CD8^+$ CTL can be adoptively transferred for therapeutic purposes in individuals afflicted with HIV infection (Koup et al., 1991, *J. Exp. Med.* 174: 1593-1600; Carmichael et al., 1993, *J. Exp. Med.* 177: 249-256; and Johnson et al., 1992, *J. Exp. Med.* 175: 961-971), malaria (Hill et al., 1992, *Nature* 360: 434-439) and malignant tumours such as melanoma (Van der Brogen et al., 1991, *Science* 254: 1643-1647; and Young and Steinman 1990, *J. Exp. Med.,* 171: 1315-1332).

In other embodiments, the composition is suitable for treatment or prophylaxis of a viral, bacterial or parasitic infection. Viral infections contemplated by the present invention include, but are not restricted to, infections caused by HIV, Hepatitis, Influenza, Japanese encephalitis virus, Epstein-Barr virus and respiratory syncytial virus. Bacterial infections include, but are not restricted to, those caused by *Neisseria* species, *Meningococcal* species, *Haemophilus* species *Salmonella* species, *Streptococcal* species, *Legionella* species and *Mycobacterium* species. Parasitic infections encompassed by the invention include, but are not restricted to, those caused by *Plasmodium* species, *Schistosoma* species, *Leishmania* species, *Trypanosoma* species, *Toxoplasma* species and *Giardia* species.

In still other embodiments, the composition is designed to induce tolerance or otherwise attenuate an immune response to a target antigen. In these embodiments, the target antigen is typically associated with or responsible for a disease or condition which is suitably selected from transplant rejection, graft versus host disease, allergies, parasitic diseases, inflammatory diseases and autoimmune diseases. Examples of transplant rejection, which can be treated or prevented in accordance with the present invention, include rejections associated with transplantations bone marrow and of organs such as heart, liver, pancreas, kidney, lung, eye, skin etc. Examples of allergies include asthma, hayfever, food allergies, animal allergies, atopic dermatitis, rhinitis, allergies to insects, fish, latex allergies etc. Autoimmune diseases that can be treated or prevented by the present invention include, for example, psoriasis, systemic lupus erythematosus, myasthenia gravis, stiff-man syndrome, thyroiditis, Sydenham chorea, rheumatoid arthritis, diabetes and multiple sclerosis. Examples of inflammatory disease include Crohn's disease, colitis, chronic inflammatory eye diseases, chronic inflammatory lung diseases and chronic inflammatory liver diseases.

The effectiveness of the immunization or tolerance may be assessed using any suitable technique. For example, CTL lysis assays may be employed using stimulated splenocytes or peripheral blood mononuclear cells (PBMC) on peptide coated or recombinant virus infected cells using $^{51}$Cr or Alamar Blue™ labeled target cells. Such assays can be performed using for example primate, mouse or human cells (Allen et al., 2000, *J. Immunol.* 164(9): 4968-4978 also Woodberry et al., infra). Alternatively, the efficacy of the immunization may be monitored using one or more techniques including, but not limited to, HLA class I tetramer staining—of both fresh and stimulated PBMCs (see for example Allen et al., supra), proliferation assays (Allen et al., supra), ELISPOT assays and intracellular IFN-γ staining (Allen et al., supra), ELISA Assays—for linear B cell responses; and Western blots of cell sample expressing the synthetic polynucleotides In order that the invention may be readily understood and put into practical effect, particular preferred embodiments will now be described by way of the following non-limiting examples.

EXAMPLES

Example 1

Use of Lactulose to Improve the Efficacy of an Anti-Cancer Vaccine in a Mouse Model C57bl/6j mice were aged and sex matched A first group of mice (Group 3) were given a vaccine comprising B16F10-B7.1 high treated with IFN-γ and IFN-β, as described in International Publication No. WO 01/88097, and the cells were irradiated for 1.5 hours at $5 \times 10^7$ cells/mL. Mice received either vaccine cells alone or including an addition of 20 mg/mL solution of lactulose at 1:1 ratio to the cell suspension. The vaccine was mixed well and injected as final volume of 400 μL intraperitoneally per mouse. This resulted in a vaccine dose of $1 \times 10^7$ cells per injection including a final 10 mg/mL lactulose per vaccination in cohort (n=4) of mice receiving vaccine plus lactulose. Each mouse was vaccinated with the above cell mix per week, over a six week period. On the seventh week they were challenged with $5 \times 10^5$ live B16F10-B7.1med cells (containing no lactulose), subcutaneously on the rear.

During the course of this experiment, a second group (no lactulose; Group 2) was vaccinated weekly over a five-week period but with a irradiated (1.5 hours) B16F10B7.1high+ IFNγP at a total $1 \times 10^7$ cells in a 200 μL injection, intraperitoneally per mouse. On the sixth week, the second group also received the challenge with $5 \times 10^5$ live cells of B16F10-B7.med (no lactulose) subcutaneously. The third group of mice (control; Group 1) received no vaccine before the challenge and as usual all succumbed to the challenge with $5 \times 10^5$ live cells of B16F10-B7.1med subcutaneously. FIG. 1 shows the results of an analysis using the MedCalc software version 7.4.4.1. From the Kaplan-Meier survival curves, it is clear that the vaccine plus lactulose sugar group fared best by far with >60% survival versus ~25% in the vaccine alone group when challenged with the live melanoma cells.

In conclusion, the results from the three survival curves are significantly different from each other. All mice not receiving vaccine (Group 1) were dead by day 33 with a median survival of only 24 days, whereas the vaccinated mice (Group 2) had a median survival of 38 days and the vaccine plus lactulose group (Group 3) are unlikely to show a median survival because most of the mice continue surviving.

Example 2

A Rapid Screening Assay for Lectin-Inhibiting Agents

The inventor has established a rapid screening assay for analysing the immune-enhancing activities of various lectin-interactive agents. The assay is based on the ability to grow lymphocytes derived from the spleens of vaccinated mice in mixed lymphocyte culture (MLC) in the presence or absence of the agents. The theory behind this approach is that tumour cells secrete galectins which then kill the T lymphocytes. Hence, given that tumour cells are typically used as stimulators in MLC to promote the growth and survival of the T lymphocytes, then if the action of secreted galectins in culture is blocked with an appropriate galectin inhibitor, the number of T lymphocytes in culture should increase as compared to a corresponding culture without the inhibitor.

Protocol:

Tumour cells, either NeuD12 FVB/N 202 breast cancer cells or C57bl6J derived B16F10 melanoma cells were used as stimulators and target cells for the assays. The tumour cells used as stimulators in the MLC were prepared as outlined in WO 01/88097 to express high levels of B7 antigen and were treated with interferon γ (1000 IU/mL) for 24 h before addition of interferon β (1000 IU/mL) for a further 24-48 h. The tumour cells were grown in 35 mm diameter×6 well cell culture dishes at about $1.5 \times 10^6$ cells per well. The tumour cells, after IFN treatment, were incubated with the growth arresting drug, mitomycin C for 20-25 min in situ in the 6-well culture dishes before it was removed by washing with PBS or fresh media three times and resuspension in 4 mL of fresh complete RPMI media/10% FCS.

Lymphocytes were extracted from the spleen of vaccinated mice and passed through a 100-200 μm stainless steel mesh sieve into 5-10 mL complete RPMI media. The red blood cells were removed by centrifugation on lymphoprep and the white blood cell layer at the interface between the culture media phase and ficoll/Hypaque phase was harvested and the ficoll/Hypaque removed by washing. The splenic derived cells were then seeded out onto the surface of the tumour cell monolayer lawns attached across the surfaces of the culture dishes. About $2 \times 10^6$ splenic lymphocytes in 1 mL complete media were added to the 4 mL of media containing growth arrested tumour cells in each well. Hence, the total number of cells per well did not exceed $1 \times 10^6$ cells per mL of culture media. The cells were cultured in a 37° C. incubator at 5% $CO_2$. Cell counts were made using the Trypan Blues exclusion dye to determine the changes occurring in the ratio of live/dead numbers of cells in each culture well over the successive days of culture. Measurements of cell numbers were made by assaying between 2-6 wells for each sample and three replicate counts for each well. The results indicate±standard error of the mean (SEM). After 2-3 days, or as required (assessed by the colour of the media pH indicator change), half the media was carefully aspirated away from each well and replaced with fresh complete media with or without added lectin-interacting agent (e.g., a carbohydrate as disclosed for instance herein generally at about 0.1 mM to about 10 mM final concentration, typically at about 1 mM). The lymphocytes were harvested between days 3-5 from the MLC dishes, and live cells separated from dead cells on lymphoprep once again. The cells were then used in a CTL assay to determine their level of killing activity on freshly prepared target cells as described in WO 01/88097.

Example 3

Figure 2:
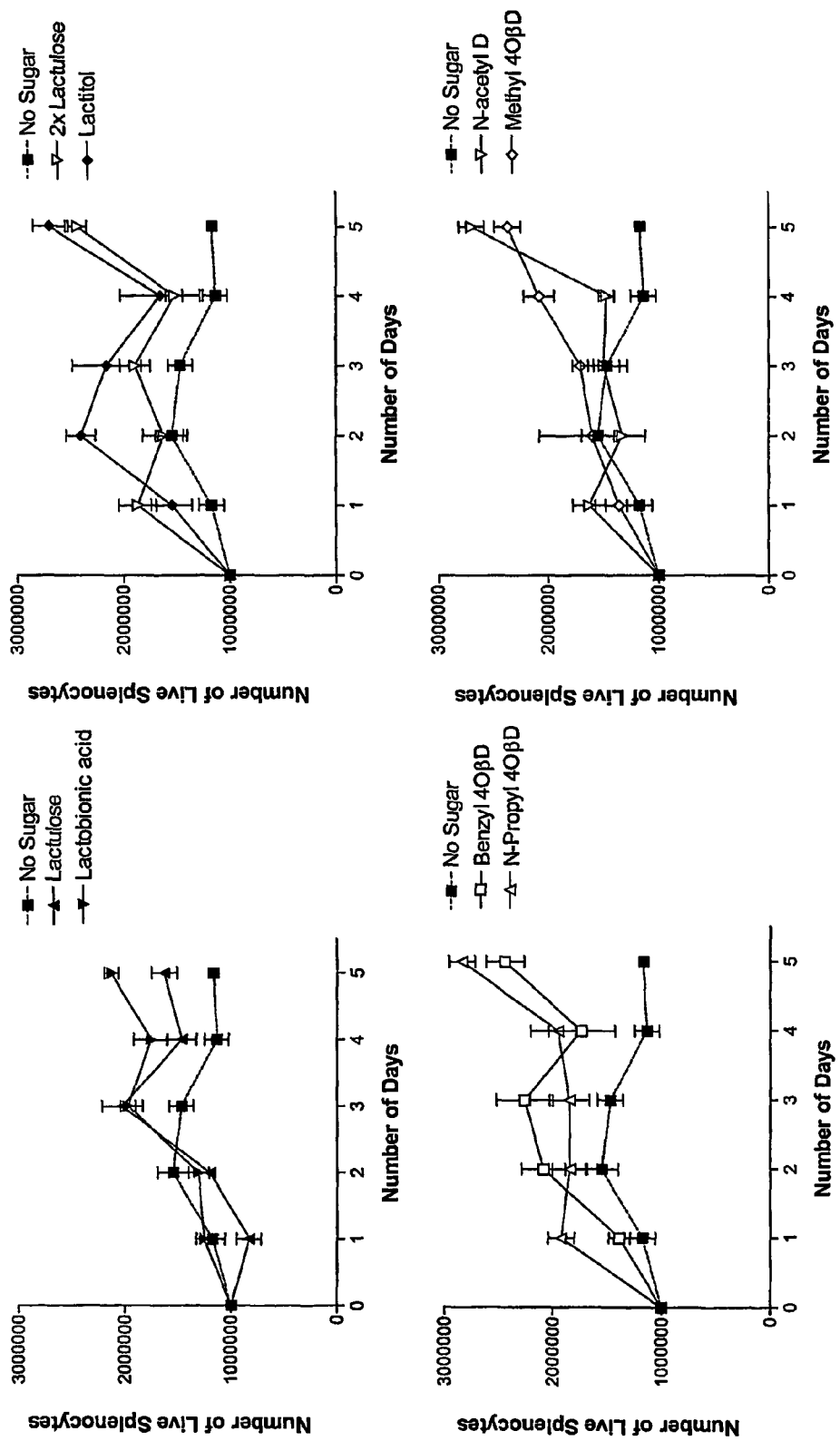
FIG. 2 is a graphical representation showing the effects of various lactose related disaccharides on the growth in culture of splenic lymphocyte populations (each having about $1\times10^6$ splenocytes), which were derived from FVB/N 202 c-neu transgenic mice vaccinated with IFN γ24 h/p48 h treated neuD12B7H4 cells (inactivated by mitomycin C treatment), in the presence of tumour cells derived from the same transgenic mice. The disaccharides tested were lactulose (at 1× and 2×), lactobionic acid (lactobionic), benzyl 4-O-13-D-galactopyranosyl-β-D-glucopyranoside (benzyl 4OβD), N-propyl-β-lactoside (N-propyl 4OβD), N-acetyl-lactosamine (N-acetyl D), and methyl 4-O-β-D-galactopyranosyl-β-D-glucopyranoside (methyl 4OβD).
Figure 3:
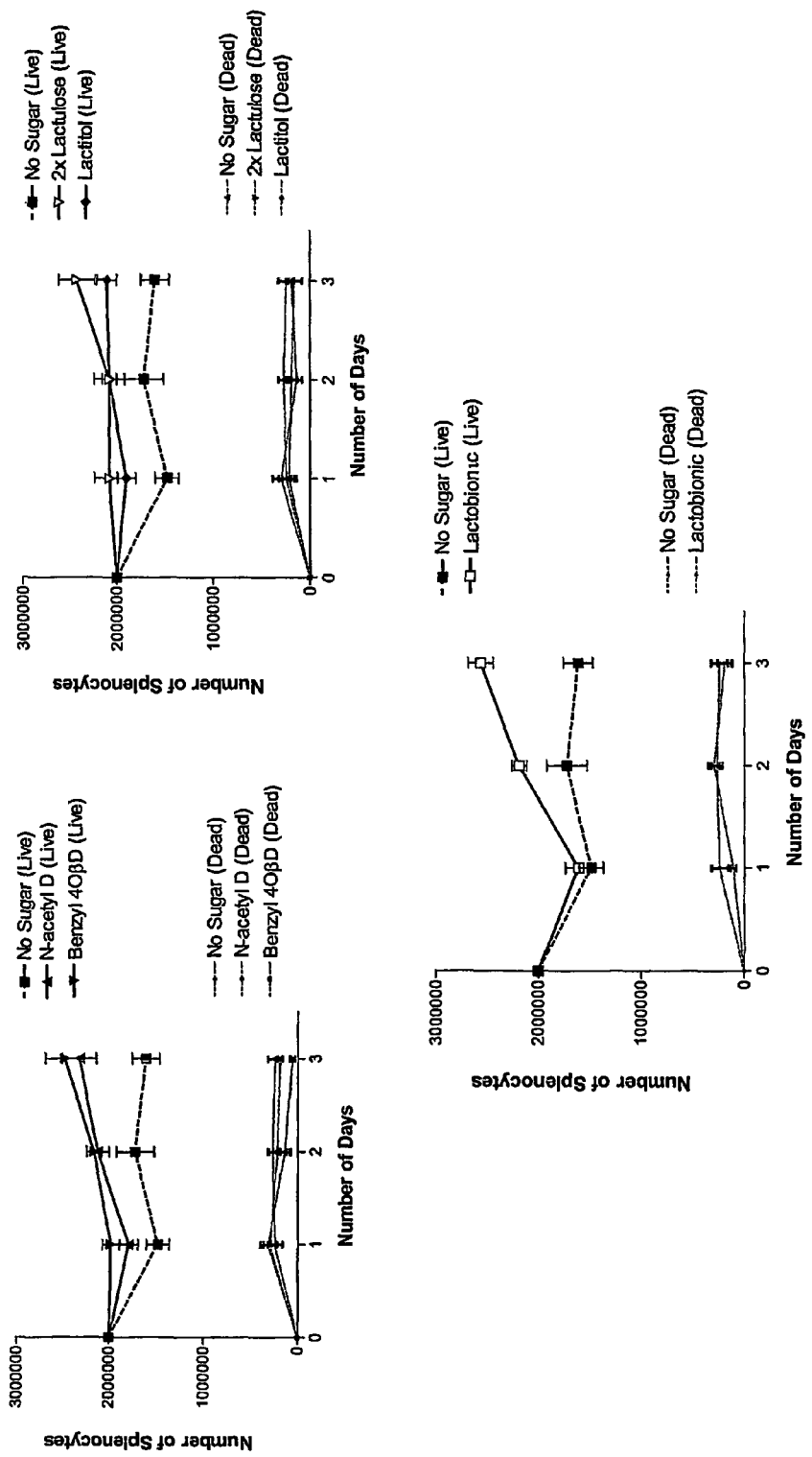
FIG. 3 is a graphical representation showing the effects of various lactose related disaccharides on the growth in culture of splenic lymphocyte populations (each having about $2\times10^6$ splenocytes), which were derived from FVB/N 202 c-neu transgenic mice vaccinated with IFN γ24 h/β48 h treated neuD12B7H4 cells (inactivated by mitomycin C treatment), in the presence of tumour cells derived from the same transgenic mice. The disaccharides tested were N-acetyl-lactosamine (N-acetyl D), benzyl 4-O-β-D-galactopyranosyl-β-D-glucopyranoside (benzyl 4OβD), lactulose, D-lactitol monohydrate (lactitol) and lactobionic acid (lactobionic).

Effect Of Different Lactose Related Disaccharides on the Growth in Culture of Splenic Lymphocyte Populations Derived from Vaccinated Mice Each of N-acetyl-lactosamine, B-lactosyl-thio-albumin, citrus pectin, D-lactitol monohydrate, lactobionic acid, benzyl 4-O-β-D-galactopyranosyl-β-D-glucopyranoside, methyl 4-O-β-D-galactopyranosyl-D-glucopyranoside, 2-methyl-β-D-galactose (1→4) D-glucose, carbomethoxyethylthioethyl 2 acetamido-2-deoxy-4-O-β-D galactopyranoyl-(3-D-glucopyranoside, carboxyethylthioethyl 2 acetamido-2-deoxy 4-O-β-D galactopyranosyl-β-D-glucopyranoside-BSA conjugate, 4-nitrophenyl 2-acetamido-2-deoxy-3-O-β-D galactopyranosyl-β-D-glucopyranoside and N-propyl-β-lactoside was added individually to the assay described in Example 2 using NeuD12 FVB/N 202 breast cancer cells as stimulators and target cells for the assay. The results from two different experiments are presented in FIGS. 2 and 3 and clearly indicate that the presence of the 1 mM concentrations of the selected lactose related sugars is superior to the absence of sugar for promoting the growth and amplification in numbers of lymphocytes in a breast cancer-specific MLC over the 3-5 days of the culture on the surface of the mitomycin C inactivated tumour cells as stimulators. Also, it appears that the differential effects become more marked in the later stages of the culture by days 4 to 5 (see FIG. 2).

Figure 4:
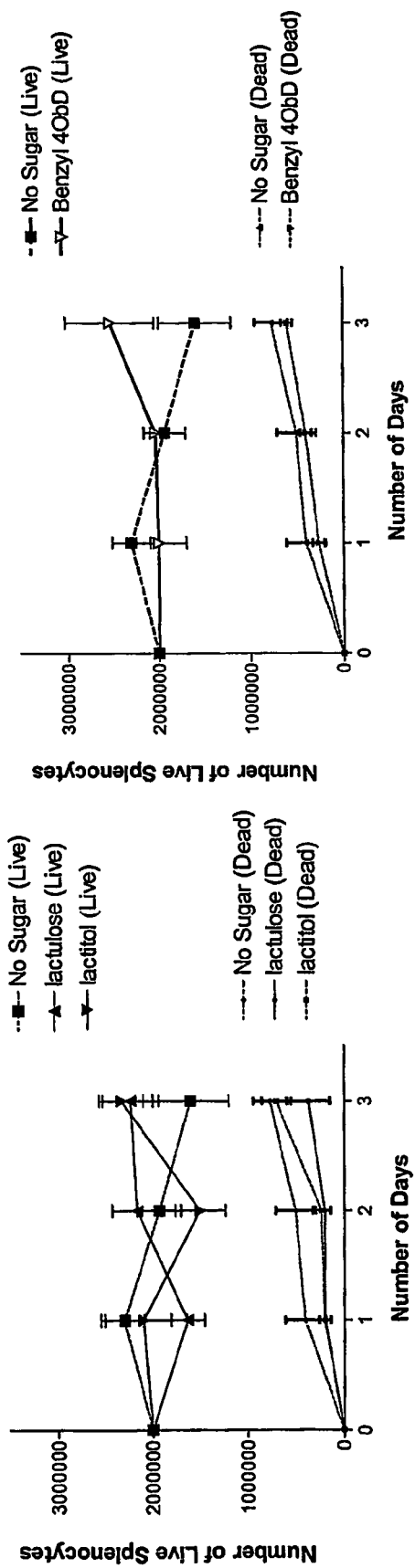
FIG. 4 is a graphical representation showing the effects of various lactose related disaccharides on the growth in culture of splenic lymphocyte populations (each having about $2 \times 10^6$ splenocytes), which were derived from C57B16J mice (melanoma mice) vaccinated with IFN γ24 h/β48 h treated B16F10B7Hi cells (inactivated by mitomycin C treatment), in the presence of tumour cells derived from the same transgenic mice. The disaccharides tested were D-lactitol monohydrate (lactitol), lactulose and benzyl 4-O-β-D-galactopyranosyl-β-D-glucopyranoside (benzyl 4OβD).

In a separate experiment, D-lactitol monohydrate, lactulose and benzyl 4-O-β-D-galactopyranosyl-β-D-glucopyranoside were each added to the assay described in Example 2 using C57bl6J derived B16F10 melanoma cells as stimulators and target cells for the assay. The lymphocytes were harvested at day 3 from the MLC dishes and were then used in a CTL assay to determine their level of killing activity, as described supra. The results presented in FIG. 4 are consistent with an effect of the sugars in promoting the proliferation of lymphocytes in a melanoma-specific MLC over the 3 days of growth.

Example 4

In Vivo Potential for Human Cancer Cells

The present invention has potential for use as therapeutic agents. In vivo studies of tumour growth and metastasis of human tumour cells either ectopically or orthotopically transplanted into immune compromised animals, such as nude mice, or in vivo studies employing well recognised animal models are conducted. Inhibition of growth of human tumour cells transplanted into immune compromised mice provide pre-clinical data for clinical trials. In vivo studies include two human tumour cell models, the metastatic non-oestrogen responsive MDA-MB-35 mammary cancer model, and the androgen non-responsive PC-3 prostate cancer model.

MDA-MB435 Mammary Cancer Model:

Pathogen free MDA-MB435 human mammary cancer cells stably transfected with a marker protein (fluorescent green protein) are grown as a solid tumour in immune compromised nude or SCID mice. The tumours are removed, and 1 mm sections of equal size are orthotopically transplanted into the mammary fat pad or ectopically transplanted into the hind flank of female nude mice. Tumour growth, metastasis, and death of the animals are determined. Tumour growth is measured by caliper evaluations of tumour size. At the time of sacrifice, tumours are removed, measured for size, and used for histochemical examination. Organs such as spleen, lymph nodes, lungs, and bone marrow, are examined for metastatic MDA-MB435 cells by histochemical staining of tissue sections for expression of the marker fluorescent green protein.

PC-3 Prostate Cancer Model:

Pathogen free PC-3 human prostate cancer cells stably transfected with a marker protein (fluorescent green protein) are grown as a solid tumour in nude mice. The tumours are removed, and 1 mm sections of equal size are ectopically transplanted into the hind flank of male nude mice. Tumour growth, metastasis, and death of the animals are determined. At the time of sacrifice, tumours are removed, measured for size, and used for histochemical examination. Organs such as spleen, lymph nodes, lungs and bone marrow are examined for metastatic PC-3 cells by histochemical staining of tissues for expression of the marker fluorescent green protein.

Skin Cancer Animal Model:

Skin cancer is induced in SENCAR and SKH-1 hairless mice by ultraviolet irradiation and chemical (DMBA) treatments. In addition, mice specifically expressing the oncogene Her-2/neu in skin basal cells that spontaneously develop skin cancer are used. The compounds disclosed herein, together with selected antigens, antigen-binding molecules or immune-modulating cells, are administered systemically or topically to the skin (optionally in the presence of a penetration enhancer as known in the art) daily, before and after skin cancer initiation, and development of skin papilloma formation is assessed. Control mice are treated identically except that they receive vehicle treatments administered in the same. The efficacy of these compounds in treating papilloma's as well as their ability to affect malignant conversion when supplied prior to premalignant progression is monitored.

Liver Metastatic Cancer Model:

In this model, liver tumour nodules are formed in mice following an intrasplenic injection of CT-26 cancer cells. The compounds disclosed herein, together with selected antigens, antigen-binding molecules or immune-modulating cells, are administered twenty-four hours after cell injection. The mice are monitored and assessed for survival over time. Moribund animals are appropriately sacrificed.

Example 5

Supplementation with Lectin-Inhibiting Agents

Prior to initiation of the in vivo experiments, lectin-inhibiting agents, which in the presence of a soluble or cellular antigen, exhibit the greatest amount of tumour cell killing are administered to nude, SCID, traxsgene, and other mice at varying levels to establish the highest level of compound that can be administered safely without adverse effects. The compounds are administered, together with selected antigens, antigen-binding molecules or inmmune-modulating cells, in a model-appropriate manner; e.g., orally, injections, including injections directly into the target organ, or topically. After establishing the highest level of the compounds that can be tolerated and effective administration routes, the novel compounds are administered to the mice on a daily basis, and tumour growth and progression is determined as described above.

Example 6

Polyvalent Melanoma Vaccine

A polyvalent melanoma cell vaccine (PMCV) is prepared essentially according to Chan and Morton (1998, *Sem Oncol.* 25(6):611-622; tradename Canvaxin, www.cancervax.com) with the exception that benzyl 4-O-β-D-galactopyranosyl-β-D-glucopyranoside or Modified Citrus Pectin (MCP) or a combination of these carbohydrates is/are added to the inoculum and BCG is not given as an adjuvant. Briefly, this vaccine comprises an allogeneic, whole-cell based vaccine containing an equal mixture of three cell lines originating from different patients. The cells are irradiated to stop them replicating, before they are cryopreserved with 0.05-10% w/v (typically 1%) MCP and/or 0.05-5% w/v (typically 0.5%) benzyl 4-O-β-D-galactopyranosyl-β-D-glucopyranoside, 5% DMSO at $2.4 \times 10^7$ cells in 1 mL volumes as a single dose. Each dose of vaccine is thawed and injected into eight sites intradermally around the torso. The vaccine is given every 2 weeks three times. Next, the cell vaccine alone is given as monthly injections for 11 months, then once every three months four times over the second year, then every 6 months six times for a total of 5 years.

In a modification of the above protocol, the antigen-presenting functions of the above cell lines are enhanced by IFN γ priming, IFN β stimulation and optionally expression of high levels of the immunostimulatory molecule B7, as described in International Publication No. WO 01/88097.

Example 7

Prostate Cancer Vaccine

A prostate cancer vaccine is prepared essentially according to U.S. Pat. No. 6,699,483 with the exception that methyl 4-O-β-D-galactopyranosyl-β-D-glucopyranoside or Modified Citrus Pectin (MCP) or a combination of these carbohydrates is/are added to the inoculum. Briefly, an immortalised cell line derived from primary prostate tissue, namely NIH1542-CP3TX, is grown in roller bottle culture in KSFM medium supplemented with 25 µg/mL bovine pituitary extract, 5 ng/Mlle of epidermal growth factor, 2 mM L-glutamine, 10 mM HEPES buffer and 5% foetal calf serum (FCS) (hereinafter referred to as "modified KSFM") following recovery from liquid nitrogen stocks. After expansion in T175 static flasks the cells are seeded into roller bottles with a growth surface area of 1,700 cm² at $2-5 \times 10^7$ cells per roller bottle.

Two metastasis-derived cell lines are also used, namely LnCap and Du145 both of which can be sourced from ATCC. LnCap is grown in large surface area static flasks in RPMI medium supplemented with 10% FCS and 2 m L-glutamine following seeding at $1-10 \times 10^6$ cells per vessel and then grown to near confluence. Du145 is expanded from frozen stocks in static flasks and then seeded into 850 cm² roller bottles at $1-20 \times 10^7$ cells per bottle and grown to confluence in DMEM medium containing 10% FCS and 2 mM L-glutamine.

All cell lines are harvested utilising trypsin at 1× normal concentration. Following extensive washing in DMEM the cells are re-suspended at a concentration of $10-40 \times 10^6$ cells/mL and irradiated at 50-300 Gy using a $Co^{60}$ source. Following irradiation the cells are formulated in cryopreservation solution composed of 10% DMSO, 8% human serum albumin in phosphate buffered saline, 0.05-10% w/v (typically 1%) MCP and/or 0.05-5% w/v (typically 0.5%) methyl 4-O-β-D-galactopyranosyl-β-D-glucopyranoside and frozen at a cell concentration of 15-50×10$^6$ cells/mL by cooling at a rate of 1° C. per minute and then transferred into a liquid nitrogen freezer until required for use.

For vaccination, prostate cancer patients are selected on the basis of being refractory to hormone therapy with a serum PSA level of 30 ng/mL. The vaccination schedule is as follows:

| Dose Number | Cell Lines Administered |
| --- | --- |
| 1, 2 and 3 | NIH1542-CP3TX (24 × 10$^6$ cells per dose) |
| 4 and subsequent | LnCap/Du145/NIH1542 (8 × 10$^6$ cells of each cell line per dose) |

The cells are warmed gently in a water bath at 37° C. and optionally admixed with mycobacterial adjuvant prior to injection into patients. Injections are made intradermally at four injection sites into draining lymph node basins. The minimum interval between doses is two weeks, and most of the doses are given at intervals of four weeks. Prior to the first dose, and prior to some subsequent doses, the patients are tested for delayed-type hypersensitivity (DTI against the three cell lines listed in the vaccination schedule above and also against PNT2 (an immortalised normal prostate epithelial cell line sourced from ECACC) (all tests involve 0.8×10$^6$ cells with no adjuvant).

To determine if vaccination results in a specific expansion of T-cell populations that recognise antigens derived from the vaccinating cell lines, proliferation assays on T-cells can be performed following stimulation with lysates of the prostate cell lines. Whole blood are extracted at each visit to the clinic and used in a BrdU (bromodeoxyuridine) based proliferation assay as described in U.S. Pat. No. 6,699,483.

Example 8

Peptide Vaccine

Selection of Cytotoxic T Lymphocyte (CTL) and Helper T Lymphocyte (HTL) Epitopes for Inclusion in a Cancer Vaccine:

This example illustrates a procedure disclosed in International Publication No. WO01/41787 for the selection of peptide epitopes for vaccine compositions, which is modified to include the administration of lectin-interactive agents. The peptides in the composition can be in the form of a nucleic acid sequence, either single or one or more sequences (i.e., minigene) that encodes peptide(s), or may be single and/or polyepitopic peptides.

The following principles are utilised when selecting an array of epitopes for inclusion in a vaccine composition. Each of the following principles is balanced in order to make the selection.

Epitopes are selected which, upon administration, mimic immune responses that have been observed to be correlated with tumour clearance. For example, a vaccine can include 3-4 epitopes that come from at least one tumour-associated antigen (TAA). Epitopes from one TAA can be used in combination with epitopes from one or more additional TAAs to produce a vaccine that targets tumours with varying expression patterns of frequently-expressed TAAs as described, e.g., in Example 15 of WO01/41787.

Epitopes are suitably selected that have a binding affinity (IC50) of 500 nM or less, often 200 nM or less, for an HLA class I molecule, or for a class II molecule, 1000 nM or less.

Sufficient supermotif (i.e., a peptide binding specificity shared by HLA molecules encoded by two or more HLA alleles) bearing peptides, or a sufficient array of allele-specific motif bearing peptides, are selected to give broad population coverage. For example, epitopes are selected to provide at least 80% population coverage. A Monte Carlo analysis, a statistical evaluation known in the art, can be employed to assess breadth, or redundancy, of population coverage.

When selecting epitopes from cancer-related antigens it is often desirable to select analogues because a patient may have developed tolerance to the native epitope.

When creating a polyepitopic composition, e.g. a minigene, it is typically desirable to generate the smallest peptide possible that encompasses the epitopes of interest, although spacers or other flanking sequences can also be incorporated. The principles employed are often similar as those employed when selecting a peptide comprising nested epitopes. Additionally, however, upon determination of the nucleic acid sequence to be provided as a minigene, the peptide sequence encoded thereby is analysed to determine whether any "junctional epitopes" have been created. A junctional epitope is a potential HLA binding epitope, as predicted, e.g., by motif analysis. Junctional epitopes are generally to be avoided because the recipient may bind to an HLA molecule and generate an immune response to that epitope, which is not present in a native protein sequence.

CTL epitopes for inclusion in vaccine compositions are, for example, selected from those listed in Tables XXVII and XXIII-XXVI of WO01/41787. Examples of HTL epitopes that can be included in vaccine compositions are provided in Table XXXI of WO01/41787. A vaccine composition comprised of selected peptides, when administered, is safe, efficacious, and elicits an immune response that results in tumour cell killing and reduction of tumour size or mass.

Peptide Composition for Prophylacetic Uses:

Peptide vaccine compositions can be used to prevent cancer in persons who are at risk for developing a tumour. For example, a polyepitopic peptide epitope composition (or a nucleic acid from which it is expressible) containing multiple CTL and/or HTL epitopes, which are desirably selected to target greater than 80% of the population, is administered to an individual at risk for a cancer, e.g., breast cancer. The composition is provided as a single polypeptide that encompasses multiple epitopes. The vaccine is administered in an aqueous carrier comprised of Freunds Incomplete Adjuvant, 0.05-10% w/v (typically 1%) MCP and/or 0.05-5% w/v (typically 0.5%) lactulose. The dose of peptide for the initial immunisation is from about 1 to about 50,000 μg, generally 100-5,000 μg, for a 70 kg patient. The initial administration of vaccine is followed by booster dosages at 4 weeks followed by evaluation of the magnitude of the immune response in the patient, by techniques that determine the presence of epitope-specific CTL populations in a peripheral blood mononuclear cells (PBMC) sample. Additional booster doses are administered as required.

Alternatively, the polyepitopic peptide composition can be administered as a nucleic acid in accordance with methodologies known in the art.

Polyepitopic Vaccine Compositions Directed to Multiple Tumours:

In an illustrative example, HER2/neu peptide epitopes, as disclosed for example in WO01/41787, are used in conjunction with peptide epitopes from other target tumour antigens to create a vaccine composition that is useful for the treatment of various types of tumours. For example, a set of TAA epitopes can be selected that allows the targeting of most common epithelial tumours (see, e.g., Kawashima et al., 1998, *Hum. Immunol.* 59:1-14). Such a composition includes epitopes from CEA, BER-2/neu, and MAGE2/3, all of which are expressed to appreciable degrees (20-60%) in frequently found tumours such as lung, breast, and gastrointestinal tumours. The composition also includes at least one of N-acetyl-lactosamine, β-lactosyl-thio-albumin, citrus pectin, D-lactitol monohydrate, lactobionic acid, benzyl 4-O-β-D-galactopyranosyl-β-D-glucopyranoside, methyl 4-O-β-D-galactopyranosyl-β-D-glucopyranoside, 2-methyl-β-D-galactose (1→4) D-glucose, carbomethoxyethylthioethyl 2 acetamido-2-deoxy-4-O-βD galactopyranoyl-β-D-glucopyranoside, carboxyethylthioethyl 2 acetamido-2-deoxy 4-O-β-D galactopyranosyl-β-D-glucopyranoside-BSA conjugate, 4-nitrophenyl 2-acetamido-2-deoxy-3-O-β-D galactopyranosyl-β-D-glucopyranoside and N-propyl-β-lactoside at 0.05-10% w/v (typically 0.5-1%).

The composition can be provided as a single polypeptide that incorporates the multiple epitopes from the various TAAs, or can be administered as a composition comprising one or more discrete epitopes. Alternatively, the vaccine can be administered as a minigene construct or as dendritic cells which have been loaded with the peptide epitopes in vitro.

Targeting multiple tumour antigens is also important to provide coverage of a large fraction of tumours of any particular type. A single TAA is rarely expressed in the majority of tumours of a given type. For example, approximately 50% of breast tumours express CEA, 20% express MAGE3, and 30% express HER-2/neu. Thus, the use of a single antigen for immunotherapy would offer only limited patient coverage. The combination of the three TAAs, however, would address approximately 70% of breast tumours. A vaccine composition comprising epitopes from multiple tumour antigens also reduces the potential for escape mutants due to loss of expression of an individual tumour antigen.

Therapeutic Use in Cancer Patients:

Evaluation of vaccine compositions are performed to validate the efficacy of the CTL and/or HTL peptide compositions in cancer patients. The main objectives of the trials are to determine an effective dose and regimen for inducing CTLs in cancer patients, to establish the safety of inducing a CTL and/or HTL response in these patients, and to see to what extent activation of CTLs improves the clinical picture of cancer patients, as manifested by a reduction in tumour cell numbers. Such a study is designed, for example, as follows:

The studies are performed in multiple centres. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21-65, include both males and females (unless the tumour is sex-specific, e.g., breast or prostate cancer), and represent diverse ethnic backgrounds.

Induction of CLM Responses Using a Prime Boost Protocol:

A prime boost protocol can also be used for the administration of the vaccine to humans. Such a vaccine regimen may include an initial administration of, for example, naked DNA in the presence of at least one carbohydrate selected from N-acetyl-4-actosamine, β-lactosyl-thio-albumin, citrus pectin, D4-lactitol monohydrate, lactobionic acid, benzyl 4-O-β-D-galactopyranosyl-β-D-glucopyranoside, methyl 4-O-β-D-galactopyranosyl-β-D-glucopyranoside, 2-methyl-β-D-galactose (1→4) D-glucose, carbomethoxyethylthioethyl 2 acetamido-2-deoxy-4-O-βD galactopyranoyl-β-D-glucopyranoside, carboxyethylthioethyl 2 acetamido-2-deoxy 4-O-β-D galactopyranosyl-β-D-glucopyranoside-BSA conjugate, 4-nitrophenyl 2-acetamido-2-deoxy-3-O-β-D galactopyranosyl-β-D-glucopyranoside and N-propyl-β-lactoside at 0.05-10% w/v (typically 0.5-1%) followed by a boost using recombinant virus encoding the vaccine in the presence of the carbohydrate(s), or recombinant protein/polypeptide or a peptide mixture administered in the presence of the carbohydrate(s) and optionally an adjuvant.

For example, the initial immunisation can be performed using an expression vector, in the form of naked nucleic acid administered IM (or SC or ID) in the amounts of 0.5-5 mg at multiple sites and in the presence of one or more carbohydrates as mentioned above. The nucleic acid (0.1 to 1000 µg) can also be administered using a gene gun. Following an incubation period of 3-4 weeks, a booster dose is then administered. The booster can be recombinant fowlpox virus administered at a dose of $5 \times 10^7$ to $5 \times 10^9$ pfu in the presence of one or more of the carbohydrates listed above. An alternative recombinant virus, such as an MVA, canarypox, adenovirus, or adeno-associated virus, can also be used for the booster, or the polyepitopic protein or a mixture of the peptides can be administered in the presence of one or more of the above-listed carbohydrates. For evaluation of vaccine efficacy, patient blood samples are obtained before immunisation as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results will indicate that a magnitude of response sufficient to achieve protective immunity against cancer is generated.

Example 9

Administration of Vaccine Compositions Using Dendritic Cells

Vaccines comprising polypeptides or peptide can be administered using antigen-presenting cells, or "professional" APCs such as dendritic cells. In this example, antigen-pulsed DC (e.g., pulsed with crude or purified polypeptide or peptide or particulate matter such viruses or bacteria) are administered to a patient to stimulate a CTL response in vivo in the presence of at least lectin-interactive agent of the invention. In an illustrative method, dendritic cells are isolated, expanded, and pulsed with a vaccine comprising peptide CTL and/or HTL epitopes corresponding to one or more target antigens. The dendritic cells are infused back into the patient in the presence of at least carbohydrate selected from N-acetyl-lactosamine, β-lactosyl-thio-albumin, citrus pectin, D-lactitol monohydrate, lactobionic acid, benzyl 4-O-β-D-galactopyranosyl-β-D-glucopyranoside, methyl 4-O-β-D-galactopyranosyl-β-D-glucopyranoside, 2-methyl-β-D-galactose (1→4) D-glucose, carbomethoxyethylthioethyl 2 acetamido-2-deoxy-4-O-βD galactopyranoyl-β-D-glucopyranoside, carboxyethylthioethyl 2 acetamido-2-deoxy 4-O-β-D galactopyranosyl-β-D-glucopyranoside-BSA conjugate, 4-nitrophenyl 2-acetamido-2-deoxy-3-O-β-D galactopyranosyl-β-D-glucopyranoside and N-propyl-β-lactoside at 0.05-10% w/v (typically 0.5-1%) to elicit CTL and HTL responses in vivo. The induced lymphocytes then destroy or facilitate destruction of the specific target tumour cells that bear the proteins from which the epitopes in the vaccine are derived.

For example, a cocktail of epitope-bearing peptides is administered ex vivo to PBMC, or isolated DC therefrom, from the patient's blood. A pharmaceutical to facilitate harvesting of DC can be used, such as Progenipoietin™ (Monsanto, St. Louis, Mo.) or GM-CSF/IL4. After pulsing the DC with peptides and prior to reinfusion into patients, the DC are washed to remove unbound peptides.

As appreciated clinically, and readily determined by one of skill based on clinical outcomes, the number of dendritic cells reinfused into the patient can vary (see, e.g., Nature Med. 4:328, 1998; Nature Med. 2:52, 1996 and Prostate 32:272, 1997). Although $2-50 \times 10^6$ dendritic cells per patient are typically administered, larger number of dendritic cells, such as $10^7$ or $10^8$ can also be provided. Such cell populations typically contain between 50-90% dendritic cells.

In some embodiments, peptide-loaded PBMC are injected into patients without purification of the DC. For example, PBMC containing DC generated after treatment with an agent such as Progenipoietin™ are injected into patients together with the carbohydrate(s) without purification of the DC. The total number of PBMC that are administered often ranges from $10^8$ to $10^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilises 2% DC in the peripheral blood of a given patient, and that patient is to receive $5 \times 10^6$ DC, then the patient will be injected with a total of $2.5 \times 10^8$ peptide-loaded PBMC. The percent DC mobilised by an agent such as Progenipoietin™ is typically estimated to be between 2-10%, but can vary as appreciated by one of skill in the art.

Example 10

Ex Vivo Activation of CTL/HTL Responses

Alternatively, ex vivo CTL or HTL responses to a particular tumour-associated antigen can be induced by incubating in tissue culture the patient's, or genetically compatible, CTL or HTL precursor cells together with a source of antigen-presenting cells (APC), such as dendritic cells, and the appropriate immunogenic antigen (e.g., peptides or polypeptides or particulate antigen). After an appropriate incubation time (typically about 7-28 days), in which the precursor cells are activated and expanded into effector cells, the cells are infused back into the patient in the presence of at least carbohydrate selected from N-acetyl-lactosamine, β-lactosyl-thio-albumin, citrus pectin, D-lactitol monohydrate, lactobionic acid, benzyl 4-O-β-D-galactopyranosyl-β-D-glucopyranoside, methyl 4-O-β-D-galactopyranosyl-β-D-glucopyranoside, 2-methyl-β-D-galactose (1→4) D-glucose, carbomethoxyethylthioethyl 2 acetamido-2-deoxy-4-O-β-D galactopyranoyl-β-D-glucopyranoside, carboxyethylthioethyl 2 acetamido-2-deoxy 4-O-β-D galactopyranosyl-β-D-glucopyranoside-BSA conjugate, 4-nitrophenyl 2-acetamido-2-deoxy-3-O-p-D galactopyranosyl-β-D-glucopyranoside and N-propyl-β-lactoside at 0.05-10% w/v (typically 0.5-1%), where they will destroy (CTL) or facilitate destruction (HTL) of their specific target cells, i.e., tumour cells.

Example 11

Pneumococcal Vaccine

The currently available pneumococcal vaccines, which manufactured, for example, by Merck and Company, Inc. (Pneumovax 23) and Lederle Laboratories (Pnu-Immune 23), and which include 23 purified capsular polysaccharide antigens of *S. pneumoniae* (serotypes 1, 2, 3, 4, 5, 6B, 7F, 8, 9N, 9V, 10A, 11A, 12F, 14, 15B, 17F, 18C, 19A, 19F, 20, 22F, 23F, and 33F), are modified to include at least one lectin-interactive agent according to the invention. In an illustrative example, one dose (0.5 mL) of the 23-valent vaccine contains 25 μg of each capsular polysaccharide antigen dissolved in isotonic saline solution with phenol (0.25%) or thimerosal (0.01%) added as preservative, 0.05-10% w/v (typically 1%) MCP and/or 0.05-5% w/v (typically 0.5%) D-lactitol monohydrate.

Pneumococcal vaccine is administered intramuscularly or subcutaneously as one 0.5-mL dose. If desired, this vaccine may be administered at the same time as influenza vaccine (by separate injection in the other arm). Pneumococcal vaccine also may be administered concurrently with other vaccines. As is known in the art, the administration of conventional pneumococcal vaccine with combined diphtheria, tetanus, and pertussis (DTP); poliovirus; or other vaccines does not increase the severity of reactions or diminish antibody responses.

Example 12

Haempohilus B Vaccine

Conventional *H. influenzae* type b vaccines (e.g., Comvax, HibTITER, ActHIB), which are typically used for immunisation of children against invasive diseases caused by this pathogen, are modified to include 0.05-10% w/v (typically 1%) MCP and/or 0.05-5% w/v (typically 0.5%) D benzyl 4-O-β-D-galactopyranosyl-β-D-glucopyranoside. Paediatric dose regimens will vary depending on vaccine used. In an illustrative example, HibTITER so modified is administered as follows:

| Age of infant | Dosage |
| --- | --- |
| 2-6 months | 0.5 mL IM q2mo for 3 doses |
| 7-11 months | previously unvaccinated: 0.5 mL IM q2mo for 2 doses |
| 12-14 months | previously unvaccinated: 0.5 mL IM once |
| Booster dose | 0.5 mL at age 15 mo or at least 2 mo after last dose of immunisation series; if aged 15-71 mo and previously unvaccinated, 0.5 mL IM is given only once |

Example 12

Meningococcal Disease Caused by *Neisseria Meningitidis*

Meningococcal polysaccharide vaccine (50 mcg of polysaccharide from each of the four serogroups of meningococci represented in the vaccine in each 0.5 mL dose (Rx) [Menomune (thimerosal 1:10,000) (lactose 2.5 to 5 mg)]) is administered together with 0.05-10% w/v (typically 1%) MCP and/or 0.05-5% w/v (typically 0.5%) methyl 4-O-β-D-galactopyranosyl-β-D-glucopyranoside subcutaneously as a single 0.5-mL dose for both children and adults.

This vaccine may be administered concurrently with other vaccines, using separate body sites, separate syringes, and the precautions that apply to each immunising agent.

Revaccination may be indicated for persons at high risk of infection, particularly children at high risk who were first immunised before they are 4 years of age; such children should be considered for revaccination after 2 or 3 years if they remain at high risk.

Meningitis, meningococcal (prophylaxis)—Meningococcal polysaccharide vaccine is indicated for immunisation against meningococcal disease caused by *Neisseria meningitidis*, Group A, Group C, Group Y, or Group W-135.

Example 13

Influenza Vaccine

Conventional influenza vaccines (Fluvax, CSL Vaccines; Fluad, Delpharm Consultants; Fluarix, GlaxoSmithKline; Fluvirin, Medeva/Ebos Health and Science; Influvac, Solvay Pharmaceuticals; and Vaxigrip, Aventis Pasteur) for administration by deep subcutaneous or intramuscular injection are modified to include at least one lectin-interactive agent according to the invention. In an illustrative example, one dose (0.5 mL) of the influenza vaccine is modified to include 0.05-10% w/v (typically 1%) MCP and/or 0.05-5% w/v (typically 0.5%) lactulose.

Dosage requirements for the modified vaccine are dependent on the age of the individual and as outlined in the product information from the manufacturer of the conventional vaccine.

Example 14

Hepatitis A Vaccine

Conventional hepatitis A vaccines (e.g., Havrix) are modified to include 0.05-10% w/v (typically 1%) MCP and/or 0.05-5% w/v (typically 0.5%) methyl 4-O-β-D-galactopyranosyl-β-D-glucopyranoside. Primary immunisation for adults consists of a single dose of 1440 EL units in 1 mL. Primary immunisation for children and adolescents (2 through 18 years of age) includes two doses of 360 EL units/0.5 mL given 1 month apart (e.g., month 0 and month 1) A booster of 360 EL units/0.5 mL is given between 6 to 12 months.

Example 15

Hepatitis B Vaccine

Conventional hepatitis B vaccines (e.g., Recombivax HB and Engerix-B) are modified to include 0.05-10% w/v (typically 1%) MCP and/or 0.05-5% w/v (typically 0.5%) benzyl 4-O-β-D-galactopyranosyl-β-D-glucopyranoside. The deltoid muscle is the preferred site for intramuscular injection in adults. The anterolateral thigh is the recommended site for intramuscular injection in infants and young children. A suitable dosage of hepatitis B surface antigen for infants, children and adolescents is 5 mcg (0.5 mL) per dose (1 dose) and for adults is 10 mcg (1.0 mL) per dose (3 doses). at 0, 1, and 6 mo.

Example 16

Human Papilloma Virus Vaccine

Conventional HPV-16 L1 virus-like-particle vaccines (e.g., Merck Research Laboratories), comprising highly purified virus-like particles of the L1 capsid of HPV-16, are modified to include at least one lectin-interactive agent. The HPV-16 L1 polypeptide is expressed in yeast (*Saccharomyces cerevisiae*). Virus-like particles are isolated with the use of standard techniques to achieve a purity of more than 97 percent and adsorbed onto amorphous aluminum hydroxyphosphate sulfate adjuvant without preservative. In an illustrative example, the modified HPV-16 vaccine includes 40 μg of HPV-16 L1 virus-ike particles formulated in 0.05-10% w/v (typically 1%) MCP and/or 0.05-5% w/v (typically 0.5%) benzyl 4-O-β-D-galactopyranosyl-β-D-glucopyranoside, methyl 4-O-β-D-galactopyranosyl-β-D-glucopyranoside and 225 μg of aluminum adjuvant in a total carrier volume of 0.5 mL. Women receive three intramuscular injections of either HPV-16 vaccine or placebo at day 0, month 2, and month 6.

Example 17

Diphtheria, Pertussis, and Tetanus Vaccines

Conventional DTAP vaccines, which protect against diphtheria, whooping cough (pertussis), and tetanus (lockjaw), are modified to include 0.05-10% w/v (typically 1%) MCP and/or 0.05-5% w/v (typically 0.5%) methyl 4-O-β-D-galactopyranosyl-β-D-glucopyranoside. The modified DTAP vaccines are given throughout childhood at specific ages, for a total of six injections. Usually a DtaP immunisation is given at: 2 months, 4 months, 6 months, of age, 15 to 18 months, 4 to 6 and 11 to 12 years of age.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A composition for modulating an immune response to a cancer or tumor antigen, comprising a galectin interactive agent selected from the group consisting of an antibody that binds to galectin and a soluble, non-metabolizable β-galactoside in a form selected from the group consisting of monosaccharides, disaccharides, larger saccharides, synthetic carbohydrates, glycopeptides, N-acetyllactosamine derivatives, modified polysaccharides, starburst dendrimers and glycopolymers, and an immune-stimulating agent selected from the group consisting of the target antigen, a part of the target antigen that elicits an immune response against the target antigen, an antigen-binding molecule that is immuno-interactive with the target antigen and an immune-modulating cell that modulates an immune response to the target antigen, wherein the immune-stimulating agent produces a greater immune response in the presence of the galectin interactive agent than in the absence of the galectin interactive agent.

2. A composition according to claim 1, wherein the galectin interactive agent binds to a galectin expressed by the cancer or tumor.

3. A composition according to claim 1, wherein the galectin-interactive agent interacts with a galectin selected from the group consisting of galectin-1, galectin-3 and galectin-9.

4. A composition according to claim 1, wherein the β-galactoside is a synthetic carbohydrate comprising thiodigalactoside.

5. A composition according to claim 1, wherein the β-galactoside is lactulose.

6. A composition according to claim 1, wherein the β-galactoside is selected from the group consisting of methyl 2-acetamido-2-deoxy-4-O-(3-[3-carboxypropanamido]-3-deoxy-β-D-galactopyranosyl)-β-D-glucopyranoside, methyl 2-acetamido-2-deoxy-4-O-(3-[{Z}-3-carboxypropenamido]-3-deoxy-β-D-galactopyranosyl)-) β-D-glucopyranoside, methyl 2-acetamido-2-deoxy-4-O-(3-benzamido-3-deoxy-(β-D-galactopyranosyl)-β-D-glucopyranoside, methyl 2-acetamido-2-deoxy-4-O-(3-[2-carboxybenzamido]-3-deoxy- β-D-galactopyranosyl)-β-D-glucopyranoside, methyl 2-acetamido-2-deoxy-4-O-(3-[4-methoxy-2,3,5,6-tetrafluorobenzamido]-3-deoxy- β-D-galactopyranosyl)-β-D-glucopyranoside, methyl 2-acetamido-2-deoxy-4-O-(3-[2-carboxy-3,4,5,6-tetrafluorobenzamido]-3-deoxy-(β-D-galactopyranosyl)-β-D-glucopyranoside, methyl 2-acetamido-2-deoxy-4-O-(3-methane-sulfonamido-3-deoxy-β-D-galactopyranosyl)- β-D-glucopyranoside, methyl 2-acetamido-2-deoxy-4-O-(3-[4-nitrobenzene-sulfonamido]-3-deoxy- β-D-galactopyranosyl)- β-D-glucopyranoside, methyl 2-acetamido-2-deoxy-4-O-(3-phenylaminocarbonylamino-3-deoxy-β-D-galactopyranosyl)-(β-D-glucopyranoside, methyl 2-acetamido2-deoxy-4-O-(2-aminoacetamido-3-deoxy-β-D-galactopyranosyl)-β-D-glucopyranoside, and methyl 2-acetamido-2-deoxy-4-O-(3-[{2S}-2-amino-3-carboxy-propanamido]-3-deoxy-β-D-galactopyranosyl)-β-D-glucopyranoside and thiodigalactoside.

7. A composition according to claim 1, wherein the β-galactoside has a binding affinity for the galectin in the range from about $10^{-3}$ to about $10^{-9}$ M.

8. A composition according to claim 1, comprising at least two different β-galactosides.

9. A composition according to claim 8, wherein one of the β-galactosides is soluble so that it can diffuse readily through the body of an animal and wherein the other is a larger β-galactoside that is partially soluble so as to limit its diffusion from the site of delivery to the animal.

10. A composition according to claim 1, wherein the cancer or tumor antigen is in a form selected from the group consisting of a peptide, a polypeptide, a nucleic acid molecule from which any of these is expressible and an antigen-presented by an antigen-presenting cell.

11. A composition according to claim 1, wherein the cancer or tumor antigen is an antigen-presenting cell that stimulates an immune response.

12. A composition according to claim 11, wherein the antigen-presenting cell is a cell to which an immune response is required and which has been optionally modified to enhance its antigen-presenting functions.

13. A composition according to claim 11, wherein the antigen-presenting cell is modified by culturing the cell in the presence of a type II interferon (IFN) and optionally at least one type I IFN for a time and under conditions sufficient to enhance the antigen-presenting function of the cell and washing the cell to remove the IFN.

14. A composition according to claim 11, wherein the antigen-presenting cell is modified by introducing a construct into the cell from which one or more IFNs selected from a type II IFN and a type I IFN are expressible.

15. A composition according to claim 11, wherein the antigen-presenting cell is an allogeneic antigen-presenting cell or cell line that shares major and/or minor histocompatability antigens to a recipient of the composition.

16. A composition according to claim 1, wherein the cancer or tumor antigen is an immune effector cell selected from the group consisting of T lymphocytes and B lymphocytes.

17. A composition according to claim 16, wherein the T lymphocytes are selected from the group consisting of cytolytic T lymphocytes helper T lymphocytes and T regulatory cells.

18. A composition according to claim 1, wherein the immune stimulating agent is an antigen-binding molecule, which binds to or otherwise interacts with the target antigen so as to reduce its level or functional activity.

19. A composition according to claim 1, further comprising one or more immunoregulatory molecules selected from the group consisting of co-stimulatory molecules, cytokines and co-inhibitory molecules.

20. A composition according to claim 19, wherein the co-stimulatory molecules are selected from the group consisting of B7-1, B7-2, B7-3, ICAM-1 and ICAM-2.

21. A composition according to claim 19, wherein the cytokines are selected from the group consisting of interferons, granulocyte/macrophage-colony stimulating factor (GM-CSF), interleukin-10 and tumor necrosis factor α (TNF-α).

22. A composition according to claim 19, wherein the co-inhibitory molecules are selected from the group consisting of OX-2 and programmed death-1 ligand (PD-1L).

23. A composition according to claim 19, wherein the immunoregulatory molecule (s) is/are provided in soluble form.

24. A composition according to claim 19, wherein the immunoregulatory molecule (s) is/are produced intracellularly from an expression construct or vector.

25. A composition according to claim 1, further comprising an adjuvant.

26. A composition according to claim 1, further comprising a pharmaceutically acceptable carrier.

27. A method for modulating an immune response to a cancer or tumor antigen in a subject, comprising administering to the subject a composition according to claim 1.

28. A method according to claim 27, wherein the galectin interactive agent and the immune-stimulating agent are administered sequentially, separately or simultaneously.

29. A method according to claim 27, which is used for the treatment of a disease or condition associated with the presence or aberrant expression of the cancer or tumor antigen in a subject.

30. A method according to claim 29, wherein the disease or condition is treated by using a composition that stimulates or otherwise enhances an immune response to the cancer or tumor antigen.

31. A method according to claim 29, wherein the disease or condition is selected from the group consisting of a pathogenic infection, a disease characterized by immunodeficiency and a cancer or tumor.

32. A method according to claim 29, wherein the disease or condition is treated by using a composition that elicits a tolerogenic response to the cancer or tumor antigen.

33. A method according to claim 29, wherein the disease or condition is selected from the group consisting of transplant rejection, graft versus host disease, allergies, parasitic diseases, inflammatory diseases and autoimmune diseases.

34. A composition according to claim 1, wherein the β-galactoside is selected from the group consisting of methyl 2-acetamido-2-deoxy-4-O-(3-benzamido-3-deoxy-β-D-galactopyranosyl)β-D-glucopyranoside, methyl 2-acetamido-2-deoxy-4-O-(3-[2-carboxy-benzamido]-3-deoxy-β-D-galactopyranosyl)-β-D-glucopyranoside, methyl 2-acetamido-2-deoxy-4-μ-(3-[4-methoxy-2,3,5,6-tetrafluorobenzamido]-3-deoxy-β-D-galactopyranosyl)-β-D-glucopyranoside, and methyl 2-acetamido-2-deoxy-4-O-(3-[2-carboxy-3,4,5,6-tetrafluorobenzamido]-3-deoxy-β-D-galactopyranosyl)-D-glucopyranoside.

\* \* \* \* \*